United States Patent [19]

Chuba

[11] Patent Number: 5,238,651

[45] Date of Patent: Aug. 24, 1993

[54] GEL PLATES, EQUIPMENT AND KITS FOR COMBINED ELECTROPHORETIC-IMMUNOELECTROPHORETIC ANALYSIS

[75] Inventor: Joseph V. Chuba, Wayne, N.J.

[73] Assignee: New York University, New York, N.Y.

[21] Appl. No.: 555,874

[22] Filed: Jul. 23, 1990

[51] Int. Cl.⁵ .................... B01D 61/42; B01D 57/02
[52] U.S. Cl. ........................ 422/61; 422/101; 422/104; 204/299 R; 436/516
[58] Field of Search .............. 436/514, 515, 516, 149; 204/182.8, 182.7, 182.9, 299 R, 301, 183.3, 180.1; 83/679, 651, 648; 422/61, 101, 104

[56] References Cited

U.S. PATENT DOCUMENTS

| | | | |
|---|---|---|---|
| 3,499,360 | 2/1968 | Davis | 436/516 |
| 3,635,808 | 1/1972 | Elevitch | 204/182.8 |
| 3,844,918 | 10/1974 | Cawley | 436/516 |
| 3,988,230 | 10/1976 | Krotz | 204/299 R |
| 4,094,759 | 6/1978 | Ruhenstroth-Bauer et al. | 204/182.8 |
| 4,246,222 | 1/1981 | Monthony | 204/182.8 |
| 4,312,727 | 1/1982 | Shainoff | 204/182.8 |
| 4,321,119 | 3/1982 | Ambler | 204/183.3 |
| 4,329,213 | 5/1982 | Elwing | 436/516 |
| 4,337,131 | 6/1982 | Vesterberg | 204/299 R |
| 4,385,974 | 5/1983 | Shevitz | 436/516 |
| 4,417,967 | 11/1983 | Ledley | 204/182.8 |
| 4,452,901 | 6/1984 | Gordon et al. | 436/516 |
| 4,558,007 | 12/1985 | Anderson et al. | 435/26 |
| 4,575,484 | 3/1986 | Straus | 436/545 |
| 4,599,305 | 7/1986 | Witte et al. | 436/536 |
| 4,668,363 | 5/1987 | Gebott et al. | 436/516 |
| 4,713,349 | 12/1987 | Levin | 436/518 |
| 4,891,319 | 1/1990 | Roser | 435/188 |
| 4,954,236 | 9/1990 | Kushner et al. | 204/182.8 |
| 4,970,070 | 11/1990 | Raft | 435/70.21 |

OTHER PUBLICATIONS

Karinkanta, H. H.; Nieminem, E. J.; An Improved Technique for Immunofixation of Electrophoretograms, Clin. Chem., 24/9, 1639–41 (1978).

Life Technologies Inc., Catalogue and Reference Guide, 1989.

Chuba, "Microimmunoelectrophoresis with Improved Resolution", *Journal of Applied Biochemistry*, vol. 1, pp. 37–50 (1979).

Poulik, "Filter Paper Electrophoresis of Purified Diphtheria Toxoid", *Can. J. Med. Sci.*, 30:417–419 (1952).

Kohn, "An Immuno-electrophoretic Technique", *Nature*, vol. 180, 986–987 (1957).

(List continued on next page.)

*Primary Examiner*—James C. Housel
*Assistant Examiner*—Jeffrey R. Snay
*Attorney, Agent, or Firm*—Browdy and Neimark

[57] ABSTRACT

Combined electrophoretic-immunoelectrophoretic analysis is conducted using a gel plate having a plurality of preformed trenches therein dividing the plate into a number of electrophoretic tracks. Serum samples are applied to the tracks such that each pair of tracks has the same sample. After subjecting the tracks to electrophoresis, one track from each pair of matching tracks is removed for protein staining by inserting a spatula into a trench and under the track to be removed. Small dabs of high vacuum silicone stopcock grease are applied to the ends of each sidewall of the remaining gel tracks and antiserum is applied therebetween. After immunoprecipitation and staining, the removed tracks are returned to their original positions to permit exact correlation of said immunoprecipitation and electrophoresis patterns. This analysis technique may be facilitated by use of equipment which includes a plate holder, a plate holder frame, underlay inserts, left and right margin inserts, a guide bar frame, templates, spatulas and plate handling hooks, burnishing rods and applicator pens. The trenches may be formed in conventional gel plates by specially designed equipment including a trench former insert frame, a double bladed gel cutter and a gel displacement beak.

17 Claims, 10 Drawing Sheets

OTHER PUBLICATIONS

Pizzolato et al., "Immunofixation on Cellulose Acetate: An Improved Screening Method for Monoclonal Immunoglobulins", *Journal of Immunological Methods*, 26:365-368 (1979).

Alper et al., "Immunofixation Electrophresis: A Technique for the Study of Protein Polymorphism", *Vox Sang*, 17:445-452 (1969).

Grabar et al., "Methode Permettant L'Etude Conjuguee Des Proprietes Electrophoretiques et Immunochimiques D'Un Melange De Proteines, Application au Serum Sanguin", *Biochem. Biophys. Acta.*, vol. 10, 193-194 (1953).

Scheidegger, "Une micro-methode de l'immuno-electrophorese", *Int. Arch. Allergy. Appl. Immunolol.*, vol. 7, pp. 103-110 (1955).

Elek, "The Serological Analysis of Mixed Flocculating System by Means of Diffusion Gradients", *British Journal of Experimental Pathology*, 2:484-500 (1949).

Saber et al., "The Role of IFE in Identifying and Quantitating Immunoglobulins", *Clinical Lab Products*, 14(1): 21-27 (1985).

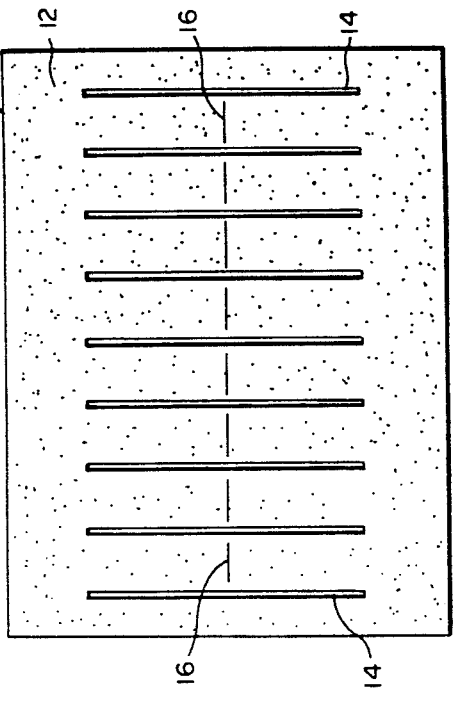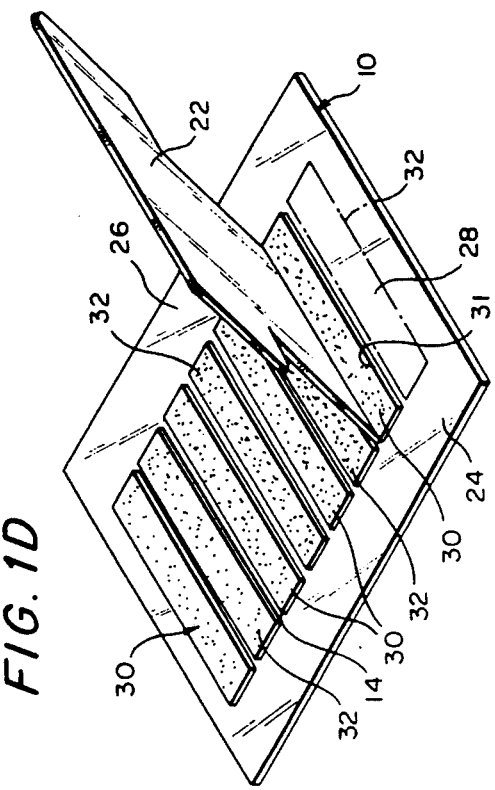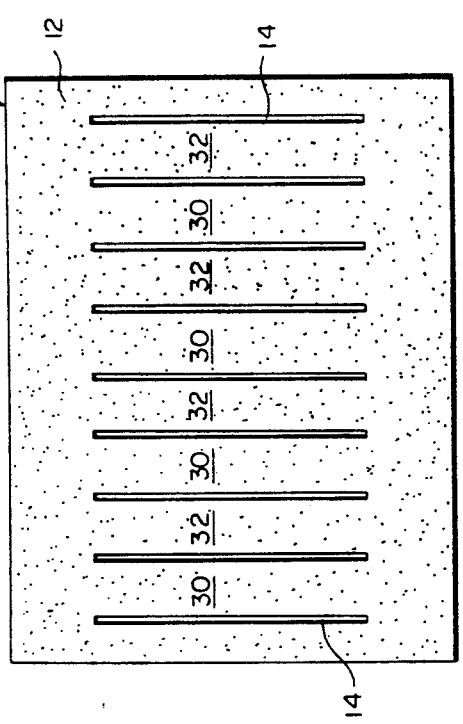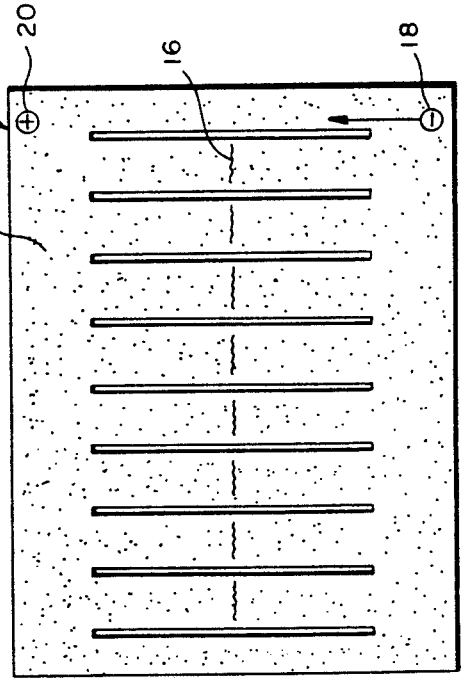

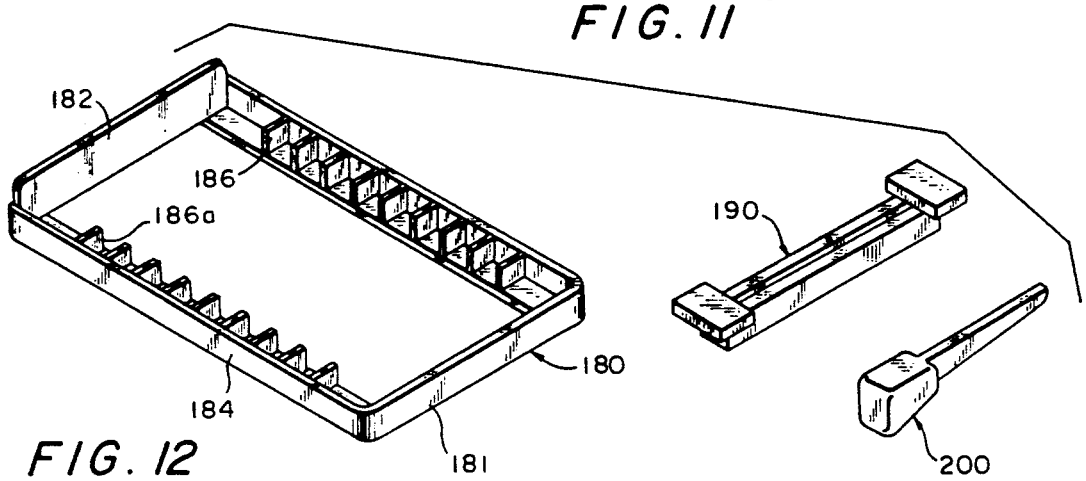
FIG. 11
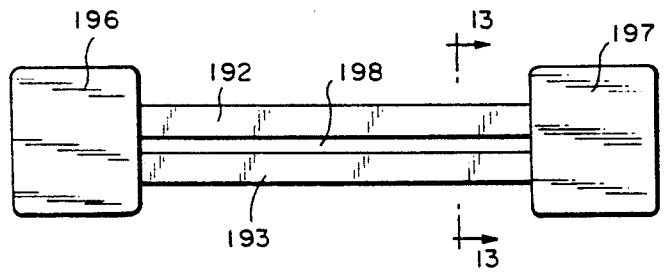
FIG. 12
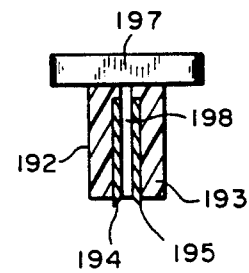
FIG. 13
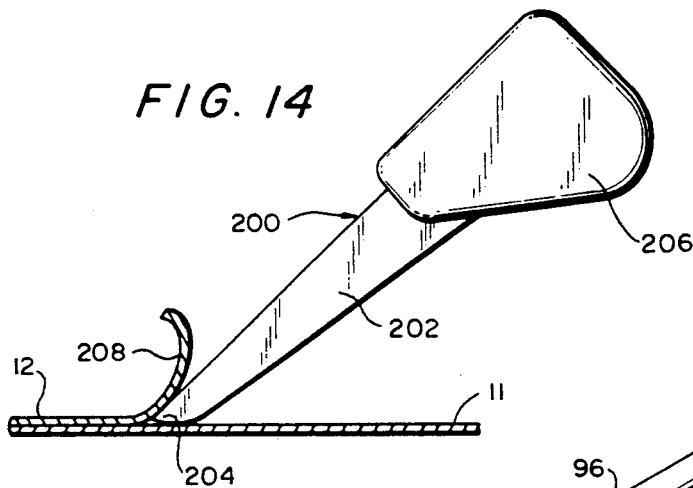
FIG. 14
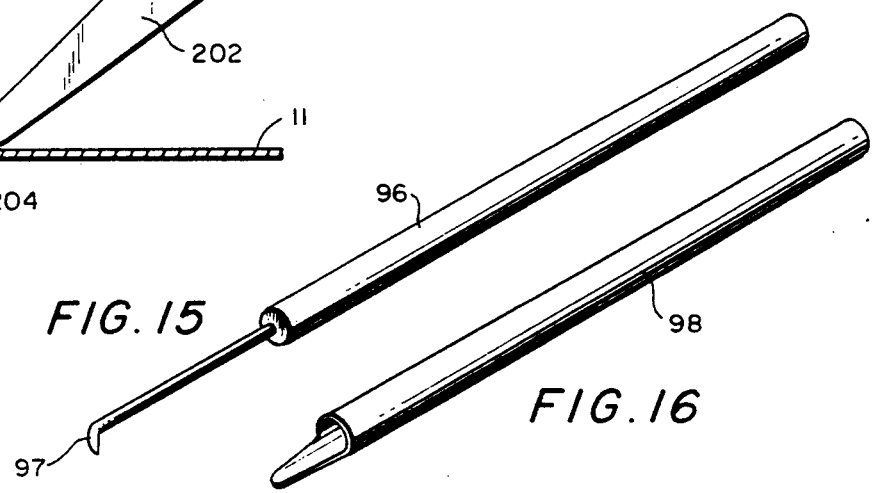
FIG. 15
FIG. 16

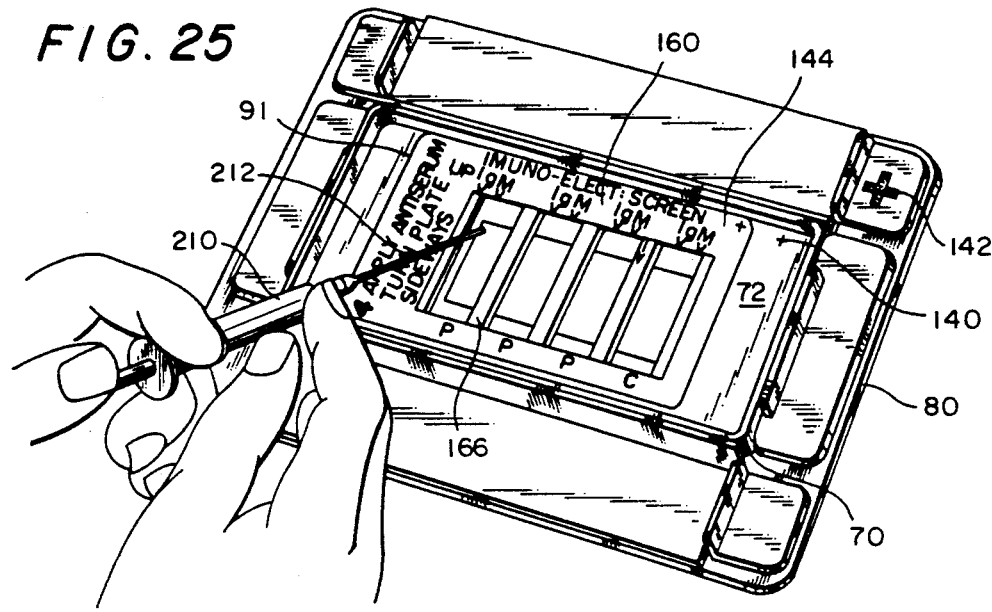
FIG. 25
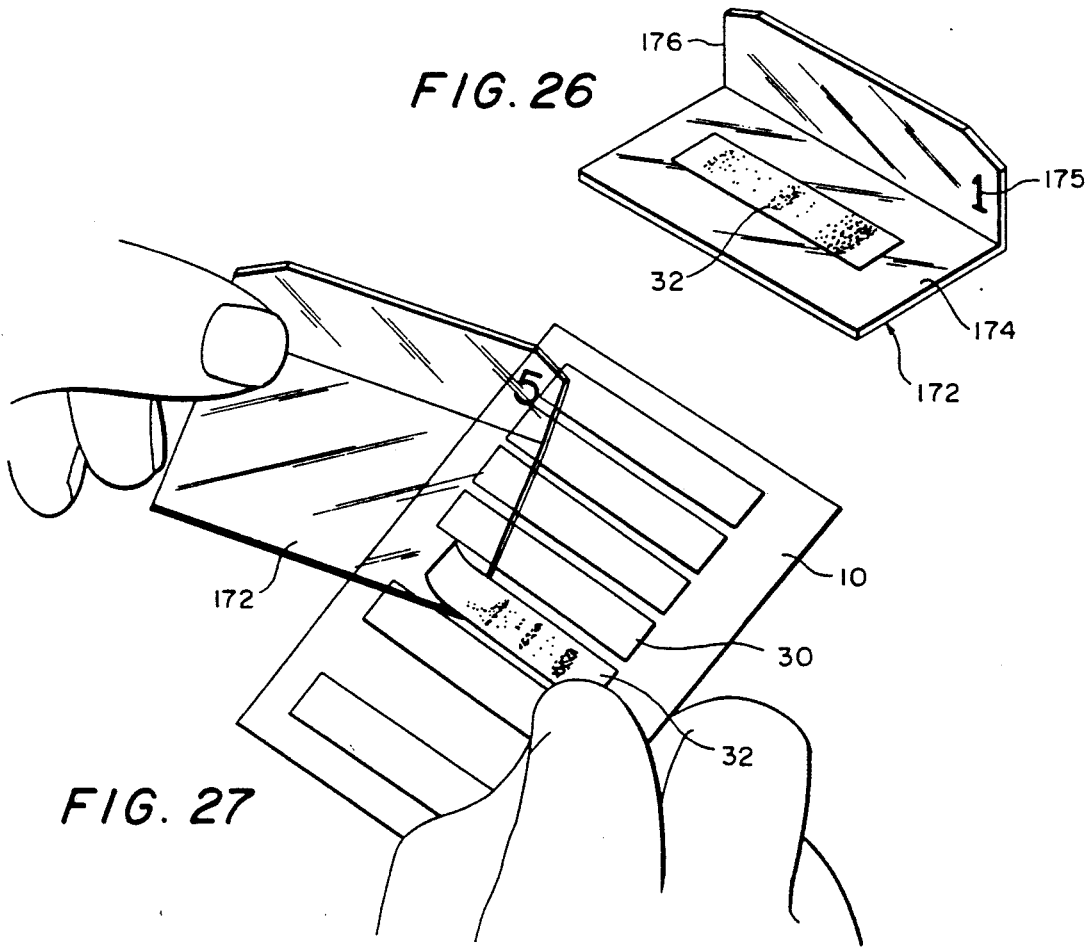
FIG. 26
FIG. 27

GEL PLATES, EQUIPMENT AND KITS FOR COMBINED ELECTROPHORETIC-IMMUNOELECTROPHORETIC ANALYSIS

FIELD OF THE INVENTION

The present invention relates to improved gel plates and improved electrophoretic-immunoelectrophoretic methods of analysis. The present invention further relates to devices for preparing such gel plates and for facilitating use thereof.

BACKGROUND OF THE INVENTION

Immunology has recently provided vast improvements in clinical analysis because of refined techniques for detecting immunological complexes. Additionally, electrophoresis has provided enhanced methods for separating molecules having similar structures.

The immunoglobulins are a heterogeneous mixture of glycoproteins the basic monomeric units of which consist of two identical heavy (H) polypeptide chains and two identical light (L) polypeptide chains joined together by interchain disulfide bonds and noncovalent forces. There are five major classes of antibodies, IgM, IgD, IgG, IgE, and IgA. The differences among these antibodies derive from the different heavy (H) chains which comprise these antibodies.

Using IgG molecules of the same IgG subclass and allotype as an example, approximately one-half of the light chains and three-fourths of the heavy chains have amino acid sequences that are identical from one IgG molecule to the next. These regions of identical amino acid sequence are referred to as the "constant regions". The remaining one-half of the light chain and one-fourth of the heavy chain is composed of highly variable amino acid sequences and is referred to as the "variable region". These regions have also been found in the other immunoglobulin classes, IgA, IgM, IgD, IgE, and are the basis for immunoglobulin classification into three structural divisions:

(1) The constant region of the heavy chains determines the class distinction. These regions have been designated gamma ($\gamma$), alpha ($\alpha$), mu ($\mu$), delta ($\delta$), and epsilon ($\epsilon$), determining IgG, IgA, IgM, IgD, and IgE, respectively.

(2) The light chain constant regions specify type and are designated kappa ($\kappa$) or lambda ($\lambda$).

(3) The variable or "idiotypic" regions of the heavy and light chains encompass the combining site or "complementarity-determining regions".

The highly variable regions of the heavy and light chains give rise to the antigen binding sites. Thus, changing the amino acid sequence in these variable regions yields antibodies with different antigenic specificities. The constant regions of the heavy chains are associated with activities such as complement fixation, cell membrane receptor interaction, passive cutaneous anaphylaxis, and transplacental transfer.

The immunoglobulins perform two functions within the immune response: recognition of antigens and initiation of a variety of secondary phenomena such as complement fixation and histamine release by mast cells. Four laboratory tests are commonly used to detect and quantify the immunoglobulins: serum protein electrophoresis (SPE), quantitation by immunodiffusion and nephelometry, immunoelectrophoresis (IEP), and immunofixation electrophoresis (IFE).

The initial step in the study of immunoglobinopathies is the SPE test. This screening procedure determines if the beta/gamma region of the pattern is abnormal in concentration or composition. A broad increase in the gamma-globulins on the electrophoretic pattern is indicative of numerous clones of plasma cells producing a heterogeneous mixture of immunoglobulins known as a polyclonal gammopathy. A polyclonal gammopathy is exhibited in a variety of clinical disorders, including autoimmune diseases, cancers, emphysema, and infections, to name a few.

Immunoelectrophoresis combines electrophoretic separation diffusion and immune precipitation of proteins. Both identification and approximate quantitation can thereby be accomplished for individual proteins present in serum, urine, or other fluid.

In the basic technique, a glass slide is covered with molten agar or agarose in a buffer solution. An antigen well and antibody trough are cut with a template cutting device. The serum sample (antigen) is placed in the antigen well and is separated in an electrical field with a potential difference of approximately 3.3 V/cm for 30-60 minutes. Antiserum is then placed into the trough, and both serum and antibodies are allowed to diffuse for up to 72 hours. The resulting precipitation lines may then be photographed or the slide washed, dried, and stained for a permanent record.

The two primary methods for classifying and typing monoclonal proteins are immunofixation and immunoelectrophoresis. In both of these methods an electrophoretic phase to separate the antigens of interest precedes the immunoprecipitation phase. Immunoelectrophoresis differs from immunofixation electrophoresis in the immunoprecipitation of the separated proteins. Immunoelectrophoresis places antibodies in a trough along the axis of electrophoretic migration. The separated antibodies and antigens are then allowed to diffuse through the support media. Where the diffusing antigen encounters the diffusing antibody, a precipitin arc is formed.

The interpretation of immunoelectrophoresis patterns depends on the comparison of arcs produced by a specimen with those produced by a normal control in the same IEP gel. Any deviations from these "normal" arcs are noted. These deviations are usually the absence or diminution of a precipitin arc, distortion of the arc in the form of thickening or bulging, or displacement of the arc from its normal position.

There are a number of immunoanalytical techniques in which a gel immunoprecipitation phase is preceded by zonal electrophoresis.

In zonal immunoprecipitation, first described by Poulik in 1952, (Poulik, M.D., Can. J. Med. Sci., 30:417-417 (1952)), zonally delineated immunoprecipitation is readily detectable in a blank layer of agar which is sandwiched between matching filterpaper strips respectively containing electrophoresed antigen (Diphtheria toxoid) and flocculating antiserum. This early study, although innovative, has been largely overlooked.

Transfer immunoelectrophoresis, described by Kohn in 1957, (Kohn, J., Nature, 180:986-987 (1957)), involved transferring a cellulose acetate zonal electrophoresis track to the surface of an agar plate, closely opposed with a parallel strip of precipitating antiserum. Formation of immunoprecipitation patterns is limited by the small amount of antiserum that can be applied via a surface strip, but can be strikingly enhanced by alternatively applying more antiserum via a conventional parallel trench.

Pizzolato et al, *J. Immunol. Methods*, 26:365–368 (1979), describe a cost-effective cellulose acetate microimmunofixation procedure.

Alper and Johnson, *Vox Sang.*, 17, 445–452 (1969), described immunofixation electrophoresis based on the same principle as Poulik's zonal immunoprecipitation, but with the antiserum applied directly to the surface of an agarose-gel electrophoresis track. Optimal predilutions of antigen must be experimentally determined for each antiserum used.

Chuba, *J. Appl. Biochem.*, 1, 37–50 (1979), proposed a double-diffusion-gradient immunoelectrophoresis using the same principles as the conventional immunoelectrophoresis of Graber and Williams, *Biochem. Biophys. Acta*, 10, 193–194 (1953) and Scheidegger, *Int. Arch. Allergy Appl. Immunol.*, 7, 103–110 (1955), but with parallel antiserum troughs much closer to, and forming a 90° angle with linear, rather than curved, fronts of antigen. In this technique, prozoning is minimized by the double diffusion gradient thus established. The prozone-minimizing effect of double immunodiffusion gradients was described by Elek, *Brit. J. Exp. Pathol.*, 2:484–500 (1949) but has largely been overlooked.

Chuba (unpublished) has also proposed a transfer immunofixation electrophoresis based upon the same principle as Alper and Johnson, supra, but wherein the zonal agarose-gel track is transferred to matching rectangular wells containing precipitating antiserum. This permits immediate staining of the remaining tracks for reference zonal protein patterns.

In immunofixation electrophoresis (IFE), the degree of band detectability is highly dependent on the appropriateness of sample predilutions relative to the potency of each antiserum. In the case of double-diffusion gradient immunoelectrophoresis (DDG-IEP), conventional immunoprecipitation lines are readily detectable with most standard grade antisera over a broad range of very low to very high concentrations of antigen.

In IFE, prozoning due to excess of antigen or antibody is maximized because of direct confrontation of antigen versus antibody, and formation of crossed or spurred immunoprecipitation lines, as seen in double immunodiffusion systems, is abrogated by the in situ immunoprecipitation. In DDG-IEP and, to a lesser extent, in conventional IEP, however, prozoning is minimized, and crossed or spurred immunoprecipitation arcs classically associated with immunologic differences between mixed components are readily ascertainable. In one-dimensional double electroimmunodiffusion, also known as countercurrent immunoelectrophoresis, counterimmunoelectrophoresis, or electroprecipitation, the basic principle involves electrophoresis in a gel medium of antigen and antibody in opposite directions simultaneously from separate wells, with resultant precipitation at a point intermediate between their origins. The principal disadvantages of double diffusion without electromotive force are the time required for precipitation, about 24 hours, and the relative lack of sensitivity. Double electroimmunodiffusion in one dimension can produce visible precipitin lines within 30 minutes, and is approximately ten times more sensitive than standard double diffusion techniques. However, this technique is only semiquantitative.

One-dimensional single electroimmunodiffusion is also known as rocket electrophoresis, or the Laurell technique. The principal application of this technique has been to quantitate antigens with faster electrophoretic mobility than immunoglobulins. In this technique, antiserum to the particular antigen or antigens one wishes to quantitate is incorporated into an agarose supporting medium on a glass slide in a fixed position so that antibody does not migrate. The specimen containing an unknown quantity of the antigen is placed into a small well. Electrophoresis of the antigen into the antibody-containing agarose is then performed. The resultant pattern of immunoprecipitation resembles a spike or rocket, which led to the term "rocket electrophoresis".

The rocket pattern occurs because precipitation occurs along the lateral margins of the moving boundary of antigen as the antigen is driven into the agar containing the antibody. Gradually, as antigen is lost through precipitation, its concentration at the leading edge diminishes, and the lateral margins converge to form a sharp point. The total distance of antigen migration for a given antiserum concentration is linearly proportionate to the antigen concentration. The sensitivity of this technique is approximately 50. micrograms/ml for proteins. Unfortunately, the weak negative charge of immunoglobulins prevents their electrophoretic mobility in this system unless special electrolytes and agar are used. Recently, several commercially available systems have been introduced for quantitating serum immunoglobulins and complement components with this technique.

Immunoelectrophoresis can aid in distinguishing polyclonal from monoclonal increases in gamma-globulin. Additionally, decreased or absent immunoglobulins observed in various immune deficiency disorders can be analyzed with this technique. However, a further quantitative analysis such as single radial diffusion, nephelometry, or radioimmunoassay should be performed for measurement of immunoglobulin levels other than in the case of electrophoretically well-delineated monoclonal bands, which can be quantitated by scanning densitometry.

Immunoelectrophoresis is also of great practical benefit in identifying abnormal immunoglobulin components, such as monoclonal Bence-Jones proteins, in the urine of patients with plasma cell dyscrasias or certain autoimmune disorders. Thus, with specific anti-kappa and anti-lambda antisera, the monoclonality of Bence-Jones protein in urine can be readily ascertained.

Antisera to "free light chains" (kappa or lambda) obtained from the urine of myeloma patients may occasionally reveal antigenic determinants not detectable on light chains "bound" to heavy chains. In H chain diseases, fragments of the immunoglobulin H chain are present in increased amounts in the serum and urine. Immunoelectrophoresis is also helpful in identifying abnormal immunoglobulin patterns (e.g., oligoclonal gamma banding) in the cerebrospinal fluid of patients with various neurologic diseases.

Immunofixation electrophoresis involves zonal separation of proteins electrophoretically in an appropriate support matrix, followed by immunoprecipitation in situ with monospecific antisera. Nonprecipitated proteins are removed by washing and the immunoprecipitation bands are revealed with a protein stain. This method has been used clinically to identify C3 conversion products and to identify paraproteins. The latter is especially helpful for low-level IgM or IgA components, which may be buried in an excess of normal IgG. There are several modifications of this basic method, such as overlay with radioactive or enzyme-linked antibodies that markedly increase the sensitivity of the method.

It can thus be seen that chemical laboratory procedures for evaluating serum and other fluids for possible presence of paraproteins are very important but are not widely enough utilized due to the difficulties and drawbacks of the present procedures.

Ideally, all immunoprecipitation patterns obtained following an initial electrophoretic separation phase should be evaluated within the context of appropriate immunoprecipitation control patterns, as well as well-delineated zonal protein reference patterns run in the same plate. In this regard, conventional immunoelectrophoresis includes normal immunoprecipitation patterns as controls in each plate, but does not provide zonal protein reference patterns. The latter, even if included in each run, would tend to be poorly delineated due to the traditional manner in which immunoelectrophoresis samples are applied via circular openings. Immunofixation electrophoresis, on the other hand, provides well-delineated zonal protein reference patterns in each plate but does not readily lend itself to the inclusion of normal immunoprecipitation control patterns.

It would be highly advantageous to have a single-plate procedure for pairing immunoelectrophoretic patterns with matching zonal protein patterns in order to provide both immunoprecipitation control patterns and well-delineated zonal protein reference patterns on the same plate.

SUMMARY OF THE INVENTION

It is an object of the present invention to overcome the above-noted deficiencies in the prior art.

It is another object of the present invention to provide a combined electrophoretic-immunoelectrophoretic analysis technique allowing single-plate pairing of immunoelectrophoretic patterns with matching zonal protein patterns.

It is a further object of the present invention to provide apparatus for conducting a combined electrophoretic-immunoelectrophoretic analysis.

It is yet another object of the present invention to provide bench equipment and kits for the quick and easy modification of conventional gel plates for use with the present invention.

It is still another object of the present invention to provide equipment and kits which facilitate carrying out the steps of the technique of the present invention easily and accurately.

According to the present invention, a modified gel plate is provided for practicing the new and improved Chuba electrophoretic-immunoelectrophoretic analysis techniques. Such a gel plate is provided with narrow, appropriately spaced trenches preformed in the gel matrix. Such preformed trenches divide the gel plate into a plurality of discrete sample tracks. The trenches may be formed in the factory at the time of production of the plates or may be formed immediately prior to use using customized trench forming equipment.

In use, the samples are applied in duplicate, as exactly matching pairs, to adjacent odd-and even-numbered sample tracks. This is accomplished by means of appropriately spaced slits in a template temporarily emplaced over the blotted gel surface. The slits evenly straddle the longitudinal sample tracks delineated by the narrow trenches. The sample aliquots are applied evenly to the template slits and then allowed to diffuse into the underlying gel matrix as discrete, blade-thin ribbons perpendicular to the intended cathodal-anodal axis of electrophoretic migration. Thus, every pair of sample tracks will have identical serum (antigen) samples thereon. The gels are then subjected to electrophoresis, following which one of each pair of tracks with identical samples is removed, preferably, by means of a specially crafted transfer spatula, and transferred for protein staining. To permit such transfer, the sample tracks are cut at their cathodal and anodal margins, at the trench extremities, and the gel material outside of the margins is removed. A plastic spatula having a width at least equal to the length of the sample track is placed in one of the trenches and gently slid under the track to be removed. Because of the width of the trench, the spatula can easily be inserted into the trench between adjacent sidewalls. The removed track on the transfer spatula is then placed in an appropriate medium for conventional protein staining. After sequential removal of one sample track from each pair of sample tracks in this manner (e.g., all of the odd-numbered sample tracks, as in FIG. 22), one is left with a plate having rectangular islands of gel, which remain firmly affixed to the gel backing.

The procedure then calls for application of precipitating antiserum of choice along each exposed longitudinal sidewall of the nontransferred sample tracks. However, it is essential for successful use of the technique that the antiserum be contained along only those segments of gel sidewall designated for double-immunodiffusion analysis. The antiserum must not "leak" around the end corners. It has been found that the antiserum can conveniently be contained along those segments by preapplying to the ends of each longitudinal sidewall a dab of a pliant hydrophobic material which will prevent the antiserum from passing but which can easily be removed when desired. The preferred material for this purpose has been found to be high-vacuum silicone stopcock grease.

After application of dabs of this pliant hydrophobic material to each end of each sidewall, the antiserum is applied to the sidewall and is unidirectionally absorbed into the delineated segments of gel sidewall by capillary action. This technique is greatly superior to the traditional antiserum trenches or special templates used to establish linear fronts of diffusing antiserum parallel to the migration pathway of the electrophoresed samples.

After appropriate incubation and staining of the immunoprecipitation patterns, the duplicate samples that had been temporarily transferred for direct protein staining are remounted on the plates in exactly their original positions. This provides a reference electrophoresis pattern and two opposing immunoprecipitation patterns for each pair of samples initially run on the same plate. This, in turn, facilitates unambiguous final interpretation of the immunoprecipitation patterns within the context of exactly corresponding electrophoresis patterns. Moreover, the dried and stained plates, appropriately annotated, permit convenient permanent documentation of the combined electrophoretic-immunoelectrophoretic findings.

Prior to the development of the improved gel plates of the present invention, a technique was employed in the laboratory of the present inventor using a conventional gel plate with ad hoc slits, rather than preformed trenches, to delineate the sample tracks. While this technique had been used commercially for several years, it has never been publicly disclosed. Furthermore, the nature of this prior technique could not be ascertained from an analysis of the stained plates which result from this method.

In this prior method, a special template is prepared having longitudinal slits. This template is used to cut slits between adjacent sample tracks. With only blade-thin slits, very careful and delicate manipulation of the special spatula was needed after the electrophoresis step to remove one track from each pair of sample tracks. The spatula blade had to be exactly placed into the slit and slid under the track to be removed without affecting the vertical sidewalls of the adjacent tracks being left. Attempting to remove the gels directly between the slits with the spatula blade often left segments of gel fragment along the gel sidewalls which then had to be delicately removed. If such fragments were left, then after removal of the transfer tracks, the edges of the remaining tracks usually had to be trimmed to restore them to a smooth vertical geometry. This caused additional problems because the sample slits must be a known fixed distance (preferably 1.5 mm) from the vertical side wall.

While this prior method usually provided excellent results when the tracks were properly removed, it was difficult and intimidating to conduct the necessary delicate manual operations. Use of the modified gel plate of the present invention with preformed trenches is a great improvement over the prior secret technique and, for the first time, permits widespread use of this technique without the necessity of intensively trained technicians.

Apparatus for facilitating the processes of the present invention has also been developed. A specially designed plate holder will hold the gel plate in place while the various operations are being conducted on it and has openings opposite the edge of the plate to facilitate removal of the plate with a device such a plate handling hook. The plate holder itself is designed to fit snugly within a plate holder frame which has marginal edges on which the hands of the operator may be rested to prevent the plate holder and the gel plate therein from moving during the various manipulations. The plate holder frame also includes a recess in the surface upon which the plate holder rests when in use. A plurality of underlay inserts are prepared of a size designed to fit within the recess and designed to be seen through the gel plate and the transparent plate holder. These underlays have areas corresponding to the areas of the gel plate which will be placed thereover and include instructions for carrying out the process of the present invention, e.g., showing which sample tracks to be removed and in what order, where to apply the dabs of stopcock grease, etc. The entire plate holder may be removed from the plate holder frame, the underlays changed, and the plate holder replaced into its place in the plate holder frame without actually touching or changing the relative position of the gel plate.

The plate holder frame also includes, as accessories, left and right margin inserts. These inserts are placed over the left and right marginal edges of the plate holder frame and include a bridge portion that extends over the side walls of the plate holder and rest on the edges of the gel plate. Thus, when the hands of the operator are resting on the edges of the left and right margin inserts, when in place on the plate holder frame, this serves to firmly hold down into place the gel plate to prevent its being scraped up from the plate holder, for example during removal of every other sample track with the transfer spatula. The plate holder frame, the left and right marginal inserts, and the underlays may be sold as a kit, along with accessories such as a plate handling hook, a burnishing rod, and an applicator pen, to provide all of the equipment needed to facilitate carrying out the process of the present invention.

An additional device for facilitating a step of the present invention is a guide bar frame which fits within the plate holder and includes transverse guide bars upon which the needle of the microdispenser may rest when streaking the designated antisera along the upper and lower sample track side walls delineated by the microdabs of stopcock grease. This guide bar frame may optionally be sold in the same kit with the plate holder, plate holder frame, etc. The guide bars are precisely spaced and beveled to permit antiserum application, via an appropriately tipped dispenser, without the dispenser tip actually touching, and possibly damaging, the gel side walls. To achieve artifact-free immunoelectrophoresis patterns at the end of the procedure, there must be absolutely no damage to the gel side walls while they are being streaked with antiserum.

A separate device for allowing the trenches to be cut into the gel plates at the laboratory bench, thereby permitting use of standard conventional gel plates without trenches, is also part of the present invention. A specially designed trench former insert frame may be placed on top of a gel plate held within a plate holder. The frame is designed to exactly fit the inside of the plate holder and, thus, always be arranged in the same relationship to the gel plate. The insert frame may be used with its own separate plate holder or it may be specially designed to be used with the plate holder used during the analysis process itself.

The trench former insert frame is designed to be used with a special double bladed gel cutter. The blades of the specially crafted gel cutter are mounted so that, when pressed into the gel to form the parallel side walls of each intended trench, the space between the blades remains completely accessible from above. This permits the insertion of a specially crafted gel-displacement beak. The beak is used to remove the narrow strip of gel between the cutter blades while the precisely positioned blades remain firmly pressed against the gel backing. Even with gels less than 1 mm thick, the device makes possible the efficient formation of multiple narrow trenches with undamaged gel side walls. Undamaged gel side walls are an absolute requirement for the proper application of antiserum in the subsequent immunodiffusion phase of the procedure.

The gel cutter is designed to fit precisely within the slots of the trench former insert frame and the slots are designed so that, when the gel cutter is placed therewithin, the trenches which are cut in the underlying gel plate will be in the exact relationship required.

The various aspects of the present invention will be better understood from a full consideration of the detailed description of preferred embodiments as illustrated in the accompanying drawings.

BRIEF DESCRIPTION OF THE DRAWINGS

FIGS. 1A to 1H show the sequence of steps of a process in accordance with the present invention, all being plan views of a gel plate at various stages of the operation, except for FIG. 1D which is a perspective view. FIG. 1A in particular shows a gel plate with preformed trenches in accordance with the present invention.

FIG. 11 is a perspective view of the components of a kit which are useful in forming precisely positioned and shaped trenches in a standard gel plate. The components include a trench former insert frame, a double bladed gel cutter and a gel displacement beak.

FIG. 12 is a plan view of a double bladed gel cutter usable with the present invention.

FIG. 13 is a cross-sectional view through lines 13—13 of the gel cutter of FIG. 12.

FIG. 14 is a side view, partially in section, showing use of a gel displacement beak of the present invention while removing a sliver of gel.

FIG. 15 is a plan view of a plate handling hook usable with the present invention.

FIG. 16 is a perspective view of an applicator pen usable in the present invention.

FIG. 25 is a perspective view showing application of antisera onto the side walls of a gel sample track held in a plate holder on a plate holder frame, using a guide bar frame and overlay insert.

FIG. 26 is a perspective view of an L-shaped transfer spatula usable with the present invention.

FIG. 27 is a perspective view showing transfer of a sample track onto a gel plate.

DETAILED DESCRIPTION OF PREFERRED EMBODIMENTS

Figure 1E:
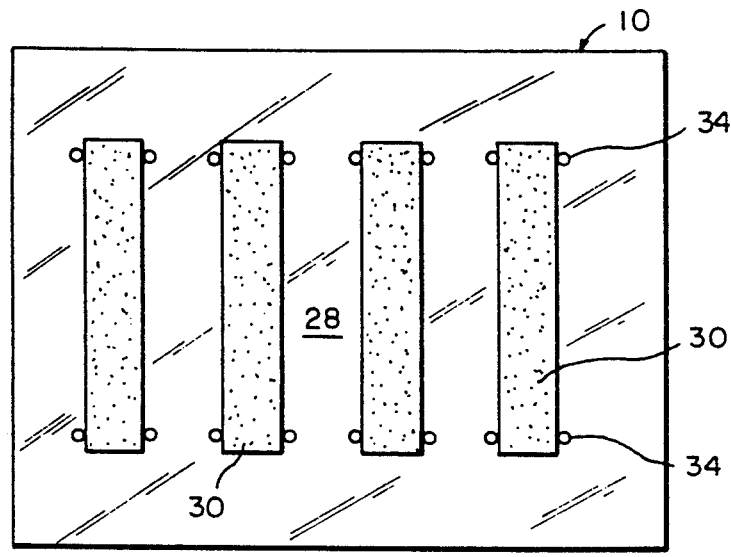

The combined electrophoretic-immunoelectrophoretic analysis technique in accordance with the present invention is preferably performed on a gel plate having preformed trenches therein, such as plate 10 shown in FIG. 1A. The plate comprises a backing sheet 11 which is substantially rigid, electrically nonconducting and non-porous, preferably of plastic or glass, (see FIG. 1D) having adhered thereto a non-sieving neutral electrophoresis matrix 12, which is preferably agarose gel. The gel matrix 12 is divided into a plurality of discrete sample tracks 30, 32 by means of appropriately spaced trenches 14. The trenches 14 are portions of the gel plate 10 in which the gel matrix 12 has been removed leaving trenches with vertical sidewalls 31 (see FIG. 1D), the bottom of which is the backing sheet 11.

In the preferred embodiment of the present invention a standard 75×100 mm gel plate, which size plate is conventionally used for the application of eight electrophoresis tracks, is used. The trenches are disposed so that each track therebetween is 10 millimeters wide with each trench having a width of 1-2 millimeter, preferably 1.5 mm.

The next step, as shown in FIG. 1B is the application of blade thin sample ribbons of serum 16 to the tracks 30 and 32 between the trenches 14. These sample ribbons are preferably administered by means of a template 50 as shown in FIG. 2. Template 50 has eight slits 52 arranged therein with a very particular geometry. Each slit 52 has a width of 7 millimeters with a distance between slits of 4 millimeters. It is very important for the immunoprecipitation process that the distance between the edge of the slit and the nearest trench side wall be a fixed distance, preferably 1.5 millimeters. Thus, the template 50 is carefully disposed over the plate 10 with preformed trenches 14 so that the slits 52 of the template 50 are exactly centered between the trenches 14 that are adjacent to the sample tracks to which antiserum is to be applied.

Figure 2:
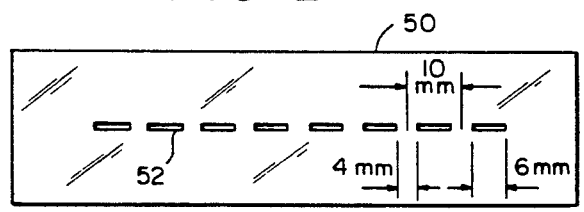
FIG. 2 is a plan view of a template which may be used in one of the steps of the present invention.
Figure 2A:
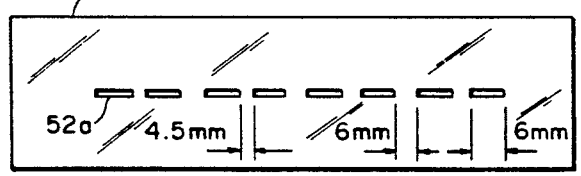
FIG. 2A is a plan view of a template which may be used in a preferred embodiment of the present invention.

Other formats employing different-width sample application slits and spacing between sample tracks may, of course, be utilized and may, indeed, be preferred. While it is very important for the immunoprecipitation process that the format provide gel margins of uniform width, preferably 1.5 mm, between the electrophoresed protein bands within the gel matrix and each adjacent sample track sidewall along which antiserum is to be applied, it is not critical to have precise placement of the slits on the reference tracks. Thus, the reference tracks may be wider than 10 mm, if desired, or arranged so as to be placed closer to their corresponding immunoprecipitation tracks. FIG. 2A shows a preferred example in which the template slits have a width of 6 mm with a distance between slits of a corresponding pair of 4.5 mm (assuming a 1.5 mm trench) and a distance between slits of differing pairs of 6 mm. Gel plates with correspondingly dimensioned trench placement (so as to have alternating tracks of 9 and 10.5 mm widths between 1.5 mm wide trenches) and corresponding underlays, not shown, would be used with this embodiment in which the paired tracks in the final product will be set off from adjacent pairs to be more easily recognizable and to ease reading of the results.

Blade-thin samples of serum are then applied through the template slits 52 to form the sample ribbons 16 on each of the eight sample tracks. Preferably every pair of sample tracks have identical samples thereon. Thus, starting from left to right in FIG. 1A, for example, tracks 30 and 32 both have the same sample applied thereto. The following tracks 30 and 32 both have the same sample thereon, which may be the same or different from those on the left-most tracks 30 and 32, and so forth. As can be seen, the template is arranged such that the sample ribbons are disposed perpendicular to and centered between the trenches.

The gel plates 10 are then subjected to electrophoresis (FIG. 1C) between cathodal margin 18 and anodal margin 20 in order to cause essentially non-sieving separation into bands along the sample tracks in accordance with differences in the isoelectric points of the component proteins.

Figure 3:
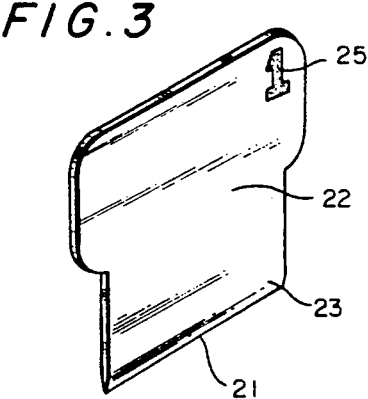
FIG. 3 is a perspective view of a transfer spatula which may be used in accordance with the present invention.

After electrophoresis, the gel along the anodal and cathodal margins is removed at 24, 26 as is the gel at the lateral margins, as shown in FIG. 1D. Sample track 32 of each pair of sample tracks is then carefully removed from the gel plate 10 and transferred to an appropriate bath for protein staining, not shown. While any appropriate spatula may be used for transferring these sample tracks, it is preferred to use a specially crafted plastic or plastic-coated transfer spatula as is shown in FIG. 3. Spatula 22 has a tapered portion 23 leading to a relatively sharp edge 21. Edge 21 of the spatula is carefully placed within the trench 14 adjacent the sample track 32 being transferred. Care is taken not to touch the vertical sidewalls 31 of the sample tracks 30 which remain. The spatula 22 is then carefully slid under the sample track 32 to be removed. When the entire sample track 32 is lying on the spatula 22 it is carried to the staining bath and transferred therein for protein staining. After the four tracks 32 have been removed, this leaves empty spaces 28 between each pair of sample tracks 30 which now remain as islands on the gel plate 10. Each island of gel has vertical side walls 31.

The next step of the process, as shown in FIG. 1E, is the application of dabs 34 of a pliant hydrophobic material which will prevent the antiserum from passing and leaking around the end corners. Microdabs 34 are placed on the sidewalls 31 of the islands 30 near the ends of each sidewall. The preferred material for preventing the antiserum from passing, and yet which can be easily removed when desired, is high vacuum silicone stopcock grease.

Figure 1F:
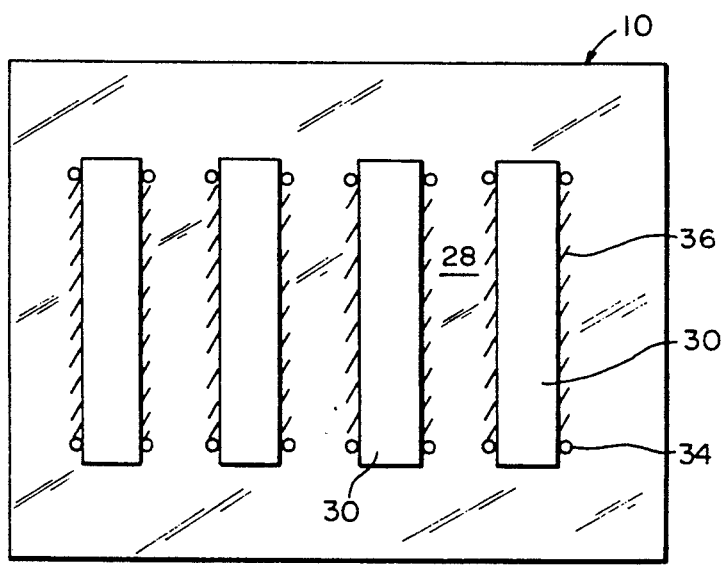

After application of the dabs 34 of this pliant hydrophobic material to each end of each sidewall, the antiserum 36 is applied to each sidewall 31 and is unidirectionally absorbed into the delineated segments of the gel sidewall by capillary action. This is shown in FIG. 1F.

Figure 1G:
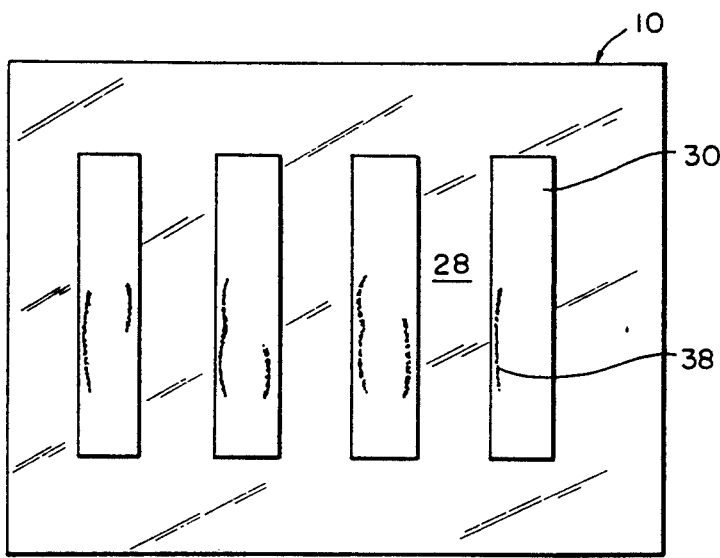
Figure 1H:
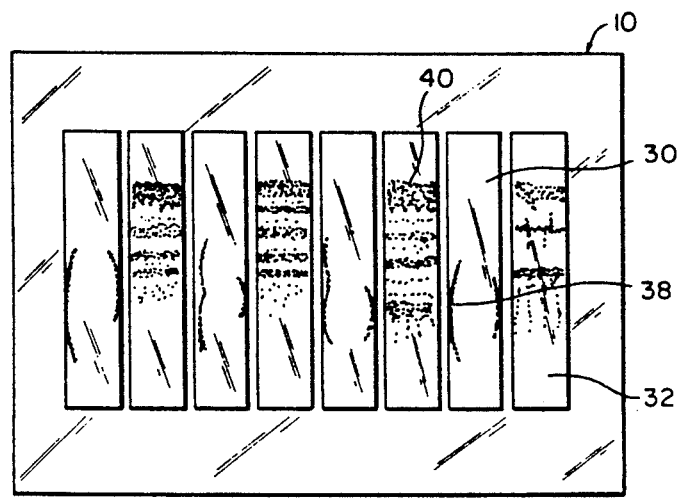

After appropriate incubation and staining, the immunoprecipitation patterns 38 become visible, as shown in FIG. 1G. The location and shape of the immunoprecipitation patterns are, of course, directly related to the location of the electrophoresis bands of serum in the sample track. In order to directly compare the immunoprecipitation patterns with the electrophoresis bands, the tracks 32 which had been removed for protein staining are replaced in the spaces 28 from which they were originally taken, as shown in FIG. 1H. The stained sample tracks 32 show the electrophoresis band patterns 40. Since the sample on the adjacent track 30 to the right of every track 32 has an electrophoresis pattern identical to that shown in track 32, an unambiguous final interpretation of the immunoprecipitation pattern within the context of exactly corresponding electrophoresis patterns is facilitated. Moreover, the dried and stained plates as shown in FIG. 1H, appropriately annotated, permit convenient permanent documentation of the combined electrophoretic-immunoelectrophoretic findings.

Figure 4:
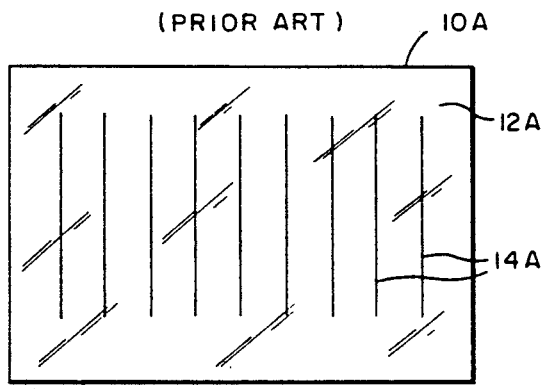
FIG. 4 is a plan view of a gel plate in accordance with the secret prior technique of the present inventor having formed slits rather than formed trenches.

An alternative embodiment of the present invention is shown in FIG. 4. This embodiment may be considered prior art in those countries in which the practice of a secret process, albeit for commercial purposes, is considered to be prior art. However, in those countries in which the practice of a process, the details of which cannot be determined from that which has been made available to the public, is not prior art, the embodiment shown in FIG. 3 and to be discussed hereinbelow is considered to be part of the present invention.

Figure 5:
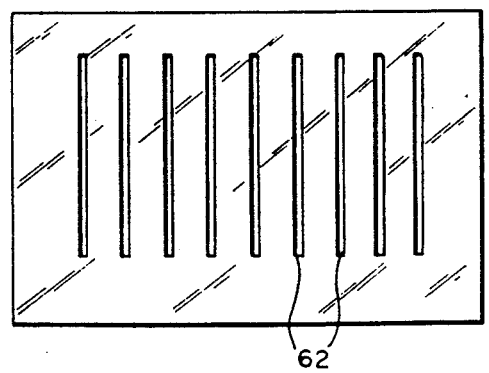
FIG. 5 is a plan view of a slit-cutting template which may be used in conjunction with the embodiment of FIG. 4.

In the embodiment shown in FIG. 4 preformed trenches are not present in the gel plate, but instead a standard fully coated gel plate coated with an electrophoresis matrix such as agarose gel is used and specially designed templates are used to place appropriate slits in the gel so that the technique of the present invention can be practiced. The standard gel plate has dimensions of 75×100 mm. A precision slit-cutting template 60 (FIG. 5) having parallel slits 62 cut therein is carefully placed on the gel plate 10A and slits are cut in the gel matrix 12A by passing a scalpel or the like through the slits 62 of the template 60 and then through the gel matrix 12A. The slits are preferably disposed 11 millimeters apart so that after the blade thin serum ribbons, having a width of 8 mm, are placed on the sample tracks there will be exactly 1.5 millimeters from the edges of these serum ribbons to the slits 14A. The template corresponding to template 50 which is used in this embodiment must be constructed slightly differently so that there will be only 3 millimeters between slits as opposed to the 4 millimeters in template 50.

After the blade thin sample ribbons of serum are applied between the slits 14A, the plate is subjected to electrophoresis as discussed above. In the next step, which comprises moving every other track for protein staining, the gel plate of this embodiment requires a very careful and delicate maneuver. The spatula 22 must be very carefully and delicately inserted exactly in the slit 14A and then slid under the sample track to be removed. Because it is critical for the subsequent immunoprecipitation step for the sidewall of the remaining islands of gel to be vertical and exactly 1.5 millimeters from the end of the sample ribbon, this procedure requires a skilled technician.

Following removal of the sample tracks which are transferred to the protein staining bath, the procedure is the same as that discussed above with respect to the preferred embodiment.

In another alternative embodiment a plate may be used which is identical to that plate of FIG. 4 except that the slits 14B are an additional millimeter apart and the template can be the same as template 50 used in the first embodiment shown in FIG. 1. The process of this embodiment is identical to the process described with respect to FIG. 3 except for the step of using the spatula 22 to remove the even numbered sample tracks for protein staining. Rather than inserting the spatula directly into the slits, the spatula is inserted approximately 1 millimeter to the right of the slits (when the plate is disposed such as is shown in FIG. 4), and the sample track removed up to the next slit. After transferring the even numbered sample tracks with the transfer spatulas, the remainder of the 1 millimeter wide strips of gel next to the slits 14A are carefully removed, such as by utilizing the squared tip of a narrow strip of filter paper. This permits a slightly less demanding insertion of the spatula but requires the additional step of the delicate removal of excess gel in order to leave the sidewall perfectly vertical and 1.5 millimeters from the serum sample ribbon. The use of the gel plate with preformed trenches of the preferred embodiment obviates the delicate and intimidating maneuvers necessary with the alternate embodiments.

Figure 6:
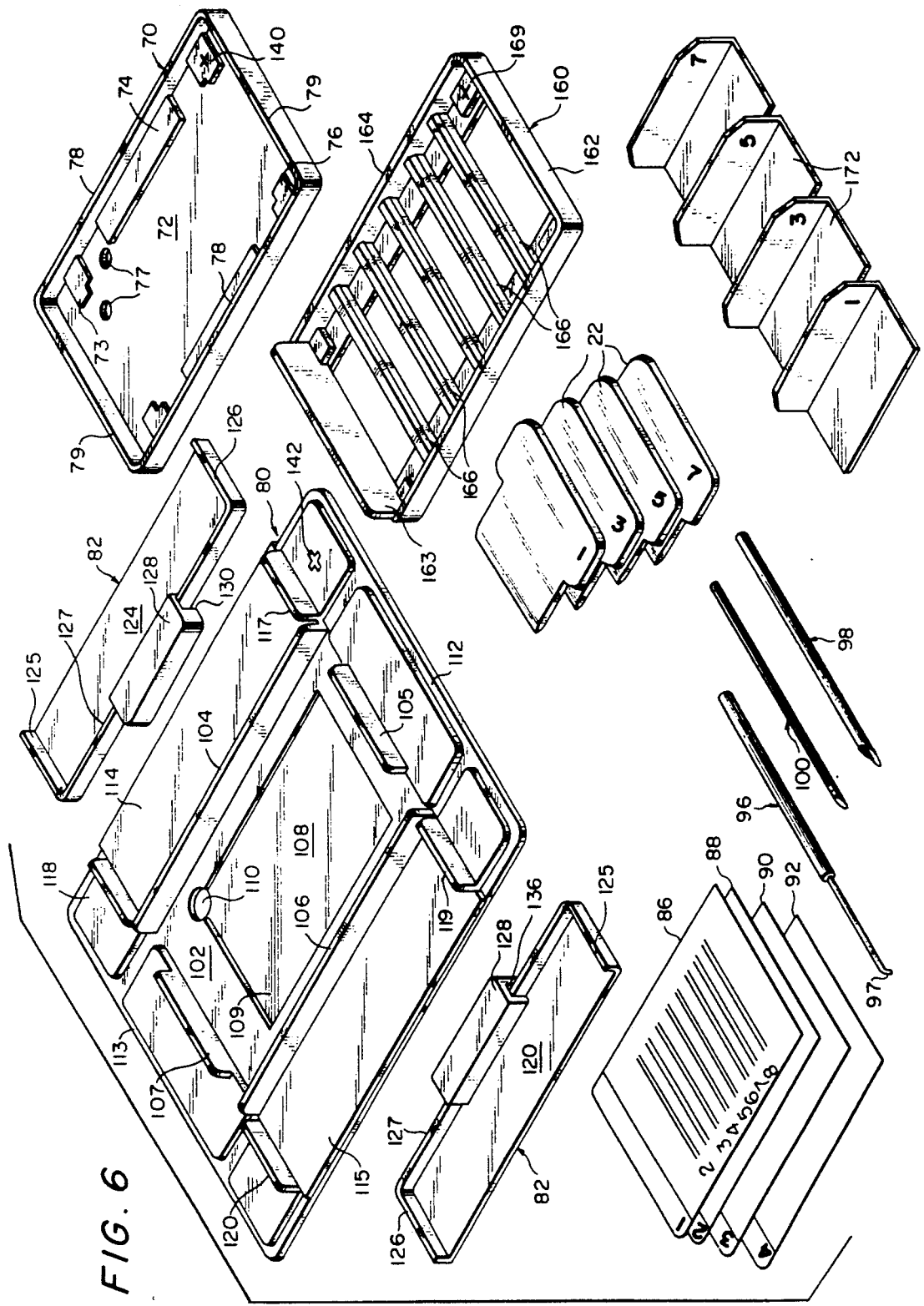
FIG. 6 is a perspective view of the components of a kit which are useful in facilitating conducting of the method of the present invention. The components include a plate holder, a plate holder frame, left and right margin inserts for the plate holder frame, a plurality of printed underlay inserts, a plate handling hook, a burnishing rod, an applicator pen, a guide bar frame, a plurality of transfer spatulas and a plurality of L-shaped transfer spatulas.
Figure 7:
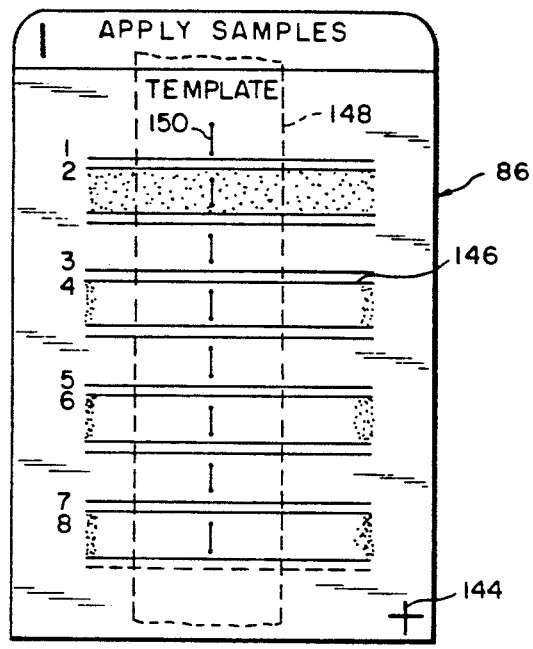
FIG. 7 is a plan view of a first underlay insert which may be used with the equipment and process of the present invention.

While the above described process can be carried out with any kind of appropriate equipment, equipment has been designed which is particularly suited for the simplification of the various steps required for carrying out the present process. This preferred equipment includes a plate holder 70 and a plate holder frame 80, as shown in FIG. 6, left and right margin inserts 82 and 84, shown in FIGS. 23 and 24, and a plurality of underlay inserts, such as inserts 86, 88, 90, and 92, shown in FIGS. 7 to 10, respectively, as well as a plate handling hook 96, an applicator pen 98, both shown in FIG. 6, and a burnishing rod 100 as shown in FIG. 15.

The plate holder 70 is designed to receive a gel plate 10 on its inner bottom surface 72. Plate guides 73, 74, 75, and 76 are disposed so as to create a space exactly equal to the size of the gel plate 10 and hold it in place, as shown, for example in FIG. 19. The edges of the gel plate 10 abut the various guide elements 73–76. Thus, once a gel plate 10 is placed into the plate holder, it cannot slide around relative to the plate holder. The plate holder 70 further includes vertical longitudinal side walls 78 and lateral side walls 79 to facilitate its maneuverability. Holes 77 are disposed on the bottom surface 72 such that the edges of the gel plate 10 will cross the openings when in place, thus facilitating the use of a plate handling hook or the like to lift the plate 10 out of the plate holder 70 when desired (see FIG. 18).

Figure 19:
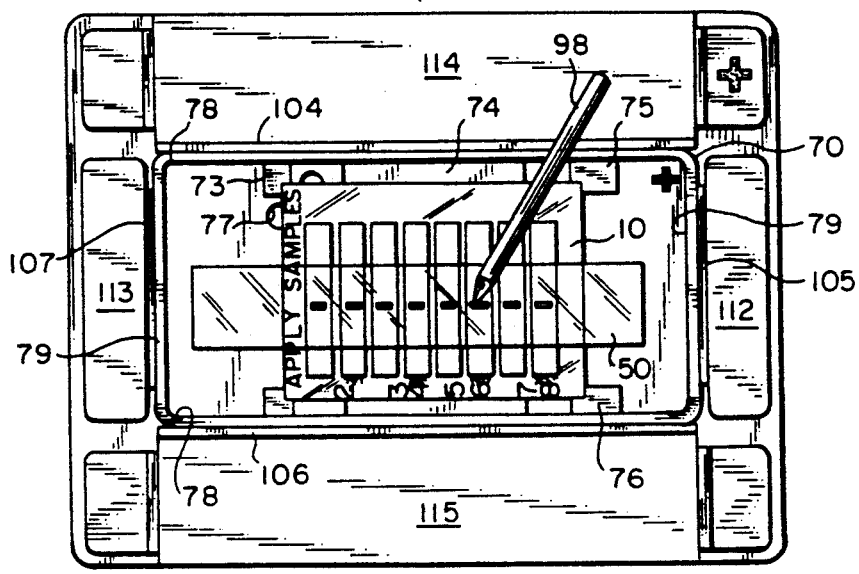
FIG. 19 is a plan view showing application of a serum sample through a sample template onto a gel plate held in a plate holder in a plate holder frame.
Figure 20:
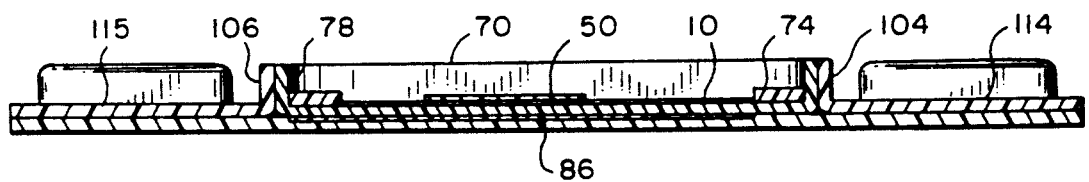
FIG. 20 is a cross-sectioned side view along lines 20—20 of FIG. 19.

The plate holder frame 80 is designed with a central bottom surface 102 between vertical side walls 104, 105, 106, and 107. The surface 102 has a size corresponding to the outer dimensions of the plate holder 70 so that the plate holder 70 may be placed therein and held in place as, for example, is shown in FIG. 19. A recess 108 is cut in the surface 102 of the plate holder frame 80 of a size designed to receive any of the various underlay inserts which will be discussed below. A floor 109 of appropriate material covers the bottom of the recess 108. An opening 110 is disposed overlapping a corner of the recess 108 and passes through the bottom surface 102 and floor 109 to facilitate removal of the underlay inserts by means of a plate handling hook, a fingernail or the like.

The plate holder frame 80 further includes lateral flanges 112, 113 and longitudinal flanges 114, 115 extending outside the plate holder surface 102. The purpose of these flanges 112–115 is to provide surfaces on which the hands of the user may be placed when performing the delicate manipulations on the gel plate 10 within the plate holder 70 when the plate holder 70 is disposed in the plate holder frame 80. This will prevent the gel plate 10 and plate holder 70 from moving with respect to the laboratory bench or other surface on which the work is being conducted.

Figure 22:
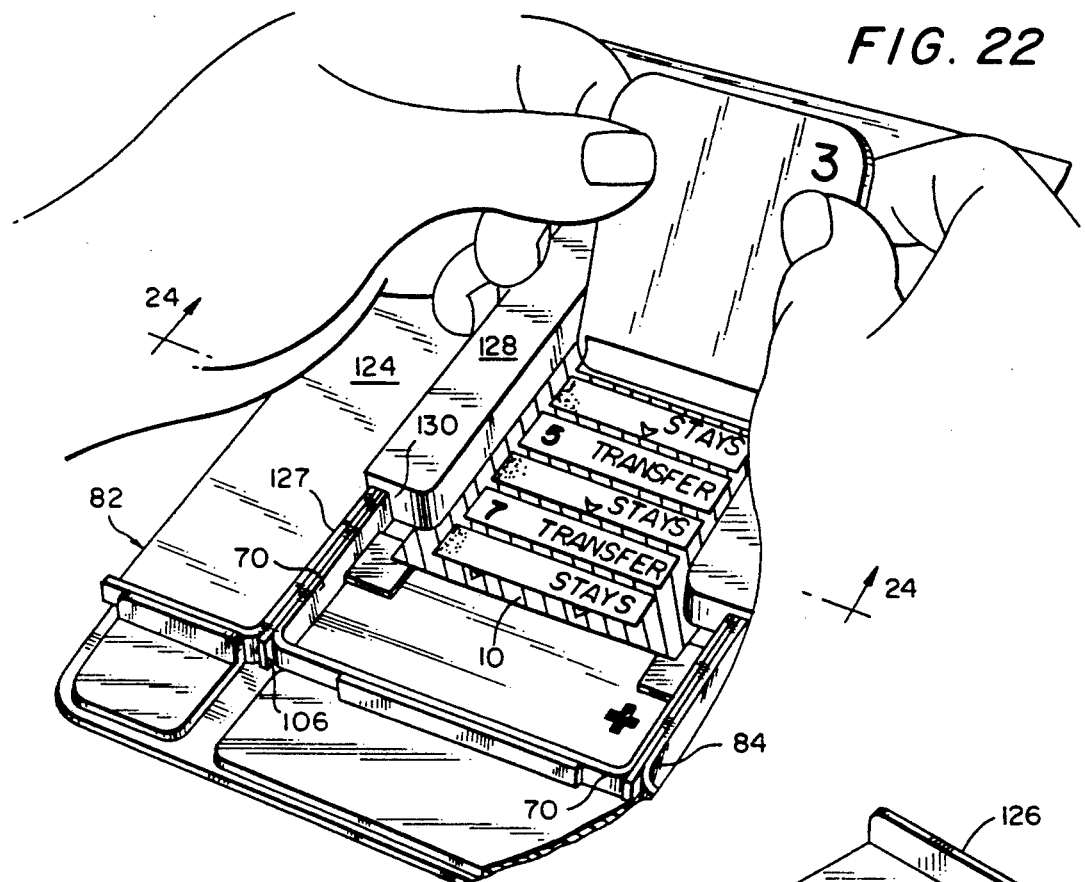
FIG. 22 is a perspective view showing the transfer of a sample track from a gel plate held in a plate holder on a plate holder frame, using left and right margin inserts.
Figure 23:
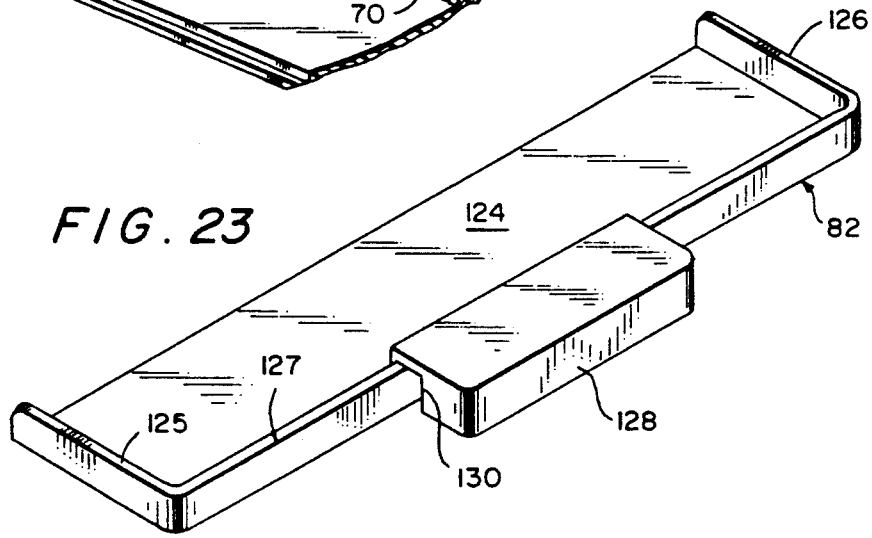
FIG. 23 is a perspective view of a left margin insert usable with the present invention.
Figure 24:
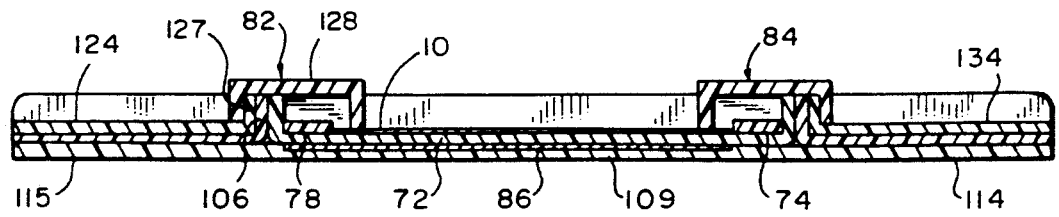
FIG. 24 is a cross-sectional view through lines 24—24 of FIG. 22.

Useful accessories to the plate holder frame 80 are the right and left margin inserts 82 and 84. Left margin insert 82 is illustrated in FIG. 23. The use of the margin inserts 82 and 84 is shown in FIGS. 22 and 24. The left margin insert 82 includes a flat surface 124 and vertical flanges 125, 126, and 127 dimensioned so as to fit precisely on the margin 115 of the plate holder frame 80 between vertical walls 119, 120 fixed to the frame 80 and vertical wall 106. The insert 82 further includes a bridge piece 128 fixedly connected thereto which is designed to rest upon the gel plate 10 when the insert 82 is in place on the marginal surface 115 of the plate holder frame 80. The bridge 128 bridges an opening 130 having the width of the combined walls 127, 106, and 78 (as shown, for example, in FIG. 22). Thus, when a gel plate 10 is disposed in the plate holder 70 and the plate holder 70 is disposed in the plate holder frame 80, as shown in FIG. 22, the left and right margin inserts 128 may be disposed on the respective marginal surfaces 115, 114 of the plate holder frame 80 with the bridge 128 extending over walls 106 of the plate holder frame 80 and 78 of the plate holder 70, so as to rest upon the gel plate 10. Thus, when the hands of the user are placed on the surfaces 124, 134 of the left and right margin inserts 82 and 84, respectively, this will serve to securely hold the gel plate 10 and plate holder 70 in place so that the various manipulative operations can be conducted without fear of movement of the surface being worked on, while still permitting the equipment to be light and portable.

The underlay inserts shown in FIGS. 7 through 10 are designed to guide the operator through various steps of the process of the present invention. For example, underlay insert 86 is used during the step discussed with respect to FIG. 1B. The template 86 is fitted into the correspondingly sized recess 109 in the bottom surface 102 of the plate holder frame 80. The plate holder 70, holding a gel plate 10, is then placed into its position on the plate holder 80, held precisely in place by the plate holder frame vertical walls 104–107. The bottom surface 72 of the plate holder 70, and preferably all surfaces of the plate holder 70 and plate holder frame 80, are constructed transparent material, such as an acrylic plastic. One corner of the plate holder 70 is preferably marked with an identifying indicia, such as a "+" 140. A corresponding indicia 142 appears in a corresponding corner of the plate holder frame 80 as well as in a corresponding corner 144 of the underlay inserts 86, 88, 90, and 92. These indicia will facilitate placement of the various parts in their proper orientation at all times.

The graphics on the underlay insert 86 include lines 146 showing the exact positioning of the sample tracks and trenches in the gel plate 10 positioned thereabove. The underlay 86 is precisely designed so that when it is placed in the recess 109 of the plate holder frame 80 and the plate holder 70 is placed thereover with the gel plate 10 being held by the plate holder 70, the drawing lines 146 are precisely below the corresponding portions of the actual gel plate 10. Insert underlay 86 also includes lines 148 drawn thereon showing the proper placement of the template 50 which is needed in order to apply the serum to the sample tracks. Template 50 may then be applied to the gel plate 10 in the plate holder 70 by lying it exactly over the lines 148 with its openings 52 exactly over the drawn openings 150 on the underlay 86, as is shown in FIG. 19.

Figure 9:
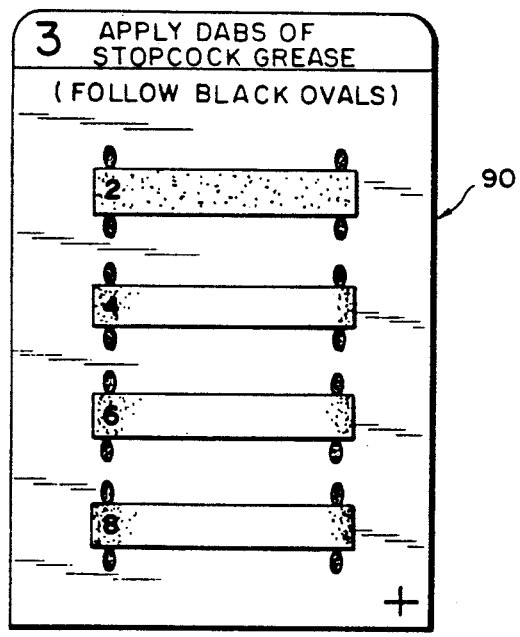
FIG. 9 is a plan view of a third underlay insert which may be used with the equipment and process of the present invention.
Figure 21:
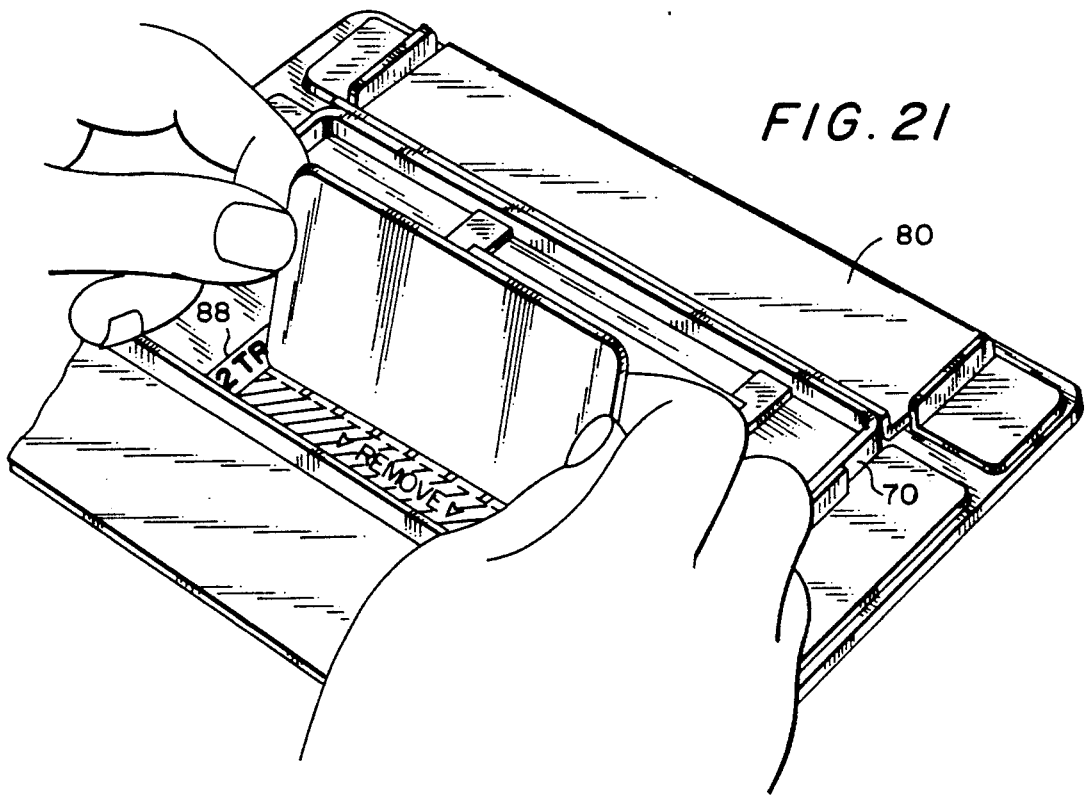
FIG. 21 is a perspective view showing the removal of a portion of gel from a gel plate held in a plate holder in a plate holder frame.

Underlay insert 88 includes graphics thereon designed to facilitate removal of the excess gel around the margins of the gel plate and the transfer of every second sample track in the manner discussed with respect to FIG. 1D hereinabove, as is shown in FIGS. 21 and 22. Underlay insert 90, shown in FIG. 9, is designed to facilitate placement of the dabs of stopcock grease as described with respect to FIG. 1E. Underlay insert 92, shown in FIG. 10, may either be used as an underlay in the same manner as inserts 86, 88, and 90, or may be used as an overlay in conjunction with the guide bar frame 160 which will be discussed below.

Another accessory which may be used with the equipment already described, in order to facilitate damage-free application of antiserum along the delicate gel side walls in the step described with respect to FIG. 1F, is the guide bar frame 160. This frame has vertical side walls 162, 163, 164, 165 which are designed to fit precisely within the walls 78, 79 of the plate holder 70. One of the vertical walls of the guide bar frame 160 may have an extension, as shown on wall 163, to facilitate removal of the guide bar frame 160 from the plate holder 70 when its function has been accomplished. An indicia 169 corresponding to indicia 140 and 142 of the plate holder 70 and plate holder frame 80 also appears on a corresponding corner of the guide bar frame 160.

The critical feature of the guide bar frame 160 is the precisely placed cross members 166 that serve as guide bars for antiserum application. These guide bars are preferably beveled, such as is shown at 168, on both of their upper corners to assist in guiding the needle or other tip of the antiserum dispenser, which will be discussed in greater detail below with respect to FIG. 25. When the side of the needle rests upon the bevels 168 of the guide bars 166, the tip of the dispensing needle may be placed closely adjacent to the side wall 31 without actually touching it. The needle may then be slid down the guide bar, permitting the needle to remain in the closely juxtaposed relationship to the side wall 31 during the application of the antisera to the entire side wall between the micro-dabs of stopcock grease.

L-shaped transfer spatulas 172, shown in FIG. 26, are also optionally part of the equipment used for practicing the process of the present invention. These L-shaped transfer spatulas 172 include a lower surface 174 and a perpendicular surface 166 which can serve as a handle. Sample tracks 32 which are removed during the step described with respect to FIG. 1D above, may be removed from a staining bath and returned to its exact placement on the gel plate 10 by means of the L-shaped transfer spatula 172 in the manner shown in FIG. 27.

All of the above described equipment for conducting the electrophoretic-immunoelectrophoretic analysis process of the present invention is preferably sold together as a kit. Thus, a plate holder 70, plate holder frame 80, left and right margin inserts 82 and 84, underlay inserts 86, 88, 90, 92 and guide bar frame 160 may all be packaged and sold together as a kit. The kit may optionally also include one or more plate handling hooks 96, applicator pens 98 and burnishing rods 100, as well as the spatulas 22, shown in FIG. 3, and the transfer spatulas 122. Templates 50 may also be included. Preferably, a plurality of each type of spatula is included so as to provide at least one type of spatula for each sample track which is to be removed. They are preferably labeled 25, 175, such as with indicia "1", "3", "5", and "7", so that the tracks do not become mixed up during the course of transferring and staining and to help assure that they are returned at the end of the process to the exact location from which they were removed earlier.

The present invention also comprehends equipment which may be used to create the trenches 14 in standard conventional gel plates. Gel plates are conventionally sold for any of a variety of analytical processes in a standard size with the gel matrix spread uniformly over the entire surface of the backing sheet. The equipment which may be provided to permit the formation of the precisely placed and dimensioned trenches 14 into such a standard gel plate at the laboratory bench includes trench former insert frame 180, double-bladed gel cutter 190, and a gel displacement beak 200. The trench former insert frame 180 includes vertical transverse walls 181, 182 and longitudinal walls 183, 184, dimensioned to fit precisely within the vertical walls 78, 79 of a plate holder 70. Instead of the plate holder 70, a specially designed plate holder may be constructed within which the trench holder insert frame 180 is designed to fit.

Two exactly matching rows of multiple slots 186 and 186a are provided within the insert frame 180. Each pair of oppositely disposed slots 186, 186a is precisely placed with respect to the position at which it is desired for a trench to be formed.

Double-bladed gel trench cutter 190, shown in more detail in FIGS. 12 and 13, includes blade support members 192 and 193 held in relative position by thumb plates 196, 197. Attached to the inside walls of the blade support members 192, 193 are cutting blades 194, 195. The cutter is designed so that the blades are held a predetermined distance apart which is equal to the width of each desired trench 14. The outside dimensions of the guide elements 192, 193 exactly match the inside dimensions of each slot 186, 186a in the trench former insert frame 180. Thus, when the gel cutter 190 is placed within a pair of slots 186, 186a, of the trench former insert frame 180, the blades 194, 195 will be disposed in the exact position over which it is desired for a trench to be cut.

It is important for the gel cutter 190 to be designed such that the space 198 between the blades 194, 195 remains completely accessible from above. This permits the insertion of the specially crafted gel displacement beak 200 into the space 198. The gel displacement beak 200 is crafted from an appropriate plastic material and includes a beak portion 202 is connected to a handle portion 206. The width of the beak 202 is exactly equal to the space between the blades 194, 195 of the gel cutter 190. The beak 202 tapers to a tip 204.

When in use, a gel plate 10 is disposed within a plate holder 70 and trench former insert frame 180 is placed within the plate holder 70. The gel cutter 190 is then placed in the first set of slots 186, 186a of the trench former insert frame 180, and the gel cutter 190 is pressed firmly down into the gel 12 of the gel plate 10, thereby forming the parallel sidewalls 31 of an intended trench 14. The space 198 between the blades 194, 195 remains accessible from above, thus permitting the insertion of the gel displacement beak 200 into space 198. While the gel cutter 190 remains firmly pressed against the gel backing 11, the beak portion 202 is placed within the opening 198 and the tapered tip 204 is slid beneath the gel 12, thereby removing a narrow strip 208 of gel between the cutter blades 194, 195. The gel cutter 190 is then removed from the first pair of slots 186, 186a in the trench former insert frame 180, and moved to the next adjacent pair of slots where the operation is repeated. Even with gels less than 1 mm thick, this equipment makes possible the efficient formation of multiple narrow trenches with undamaged vertical gel sidewalls.

The trench forming equipment 180, 190, and 200 may be sold as a separate kit, optionally with its own plate holder 70.

Besides the kit including equipment for cutting trenches in standardized gel plates and the kit including equipment to facilitate carrying out the electrophoretic-immunoelectrophoretic analysis technique of the present invention, gel plates with preformed trenches may also be packaged in the form of a kit with templates 50 and, optionally, with disposable spatulas 22 and 172. Also present may be a set of instructions informing the user how to conduct the technique of the present invention.

It should be understood that while the description of the preferred embodiments discussed above utilized conventionally dimensioned gel plates of about 75×100 mm, this is not critical for practicing the present invention and gel plates of any appropriate size and shape can be used as long as electrophoresis can be performed thereon and as long as appropriately shaped preformed trenches are present therein. Thus, rather than eight sample tracks, the gel plate may be dimensioned to have only four or as many as sixteen or more. Appropriate modification to the equipment discussed above would be readily apparent to those of ordinary skill in the art in order to adapt to any such changes in size or number of tracks.

Furthermore, while it has been stressed hereinabove that it is important that the vertical sidewalls of the gel islands on which the antiserum is placed should be 1.5 millimeters from the sample ribbons, this also is not critical as long as the distance from the sidewall to the sample ribbon is uniform for all of the sample tracks. As long as this uniformity is present, then unambiguous final interpretation of the immunoprecipitation patterns may be made, particularly after a number of reference experiments are conducted. While a width of 1.5 millimeter for the trenches is indicated as being preferred, those of ordinary skill in the art will understand that the trench can be of any width as long as it is large enough to permit insertion of the spatula blade. The maximum width is determined only by the consideration of avoiding wasted space on the gel plate. Of course, the template 50 must be designed to specifically correspond to whatever trench width is being used on the given gel plate. A trench width of about 0.5 to about 3 millimeters is probably the practical limit with the preferred width being about 1.5 millimeter.

EXAMPLE 1

Trench Formation thin-layer, 76×102 mm agarose-gel plates (Paragon SPE plates, Beckman Instruments, Brea, Calif.) were obtained for use in the microelectrophoretic-immunoelectrophoretic analysis of the present invention. The gel cutting equipment was designed so as to be able to cut eight trenches in such plates parallel to the 76 mm side dividing the plate into eight sample tracks. It is not necessary to cut a ninth trench as the last sample track (shown on the left in FIG. 1H) is not used for immunoprecipitation and does not need a precise sidewall. The gel cutter 190 is designed so that each trench is 1.5 mm wide and approximately 56 mm long, keeping about a 10 mm margin above and below the trenches to the edge of the plate. The trench former insert frame is designed such that the trenches are disposed 10 mm apart (center to center), leaving a margin of about 10.5 mm of gel on the right and left side of the plate.

Figure 17:
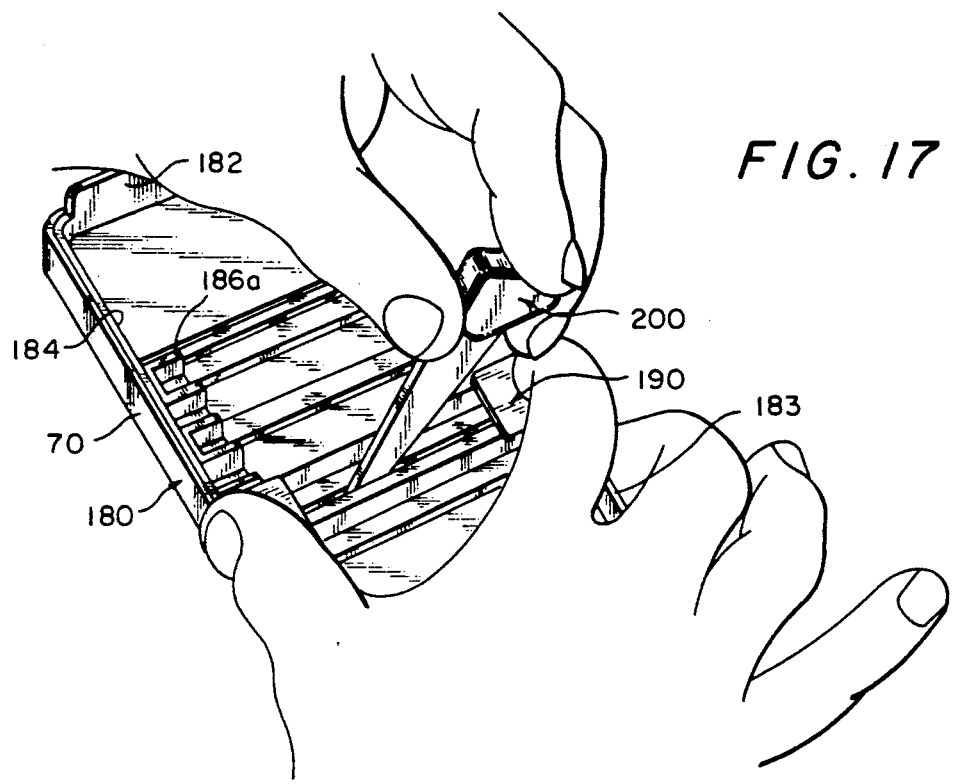
FIG. 17 is a perspective view showing use of a trench former insert frame, gel cutter, and gel displacement beak in forming trenches in a gel plate mounted on a plate holder.
Figure 18:
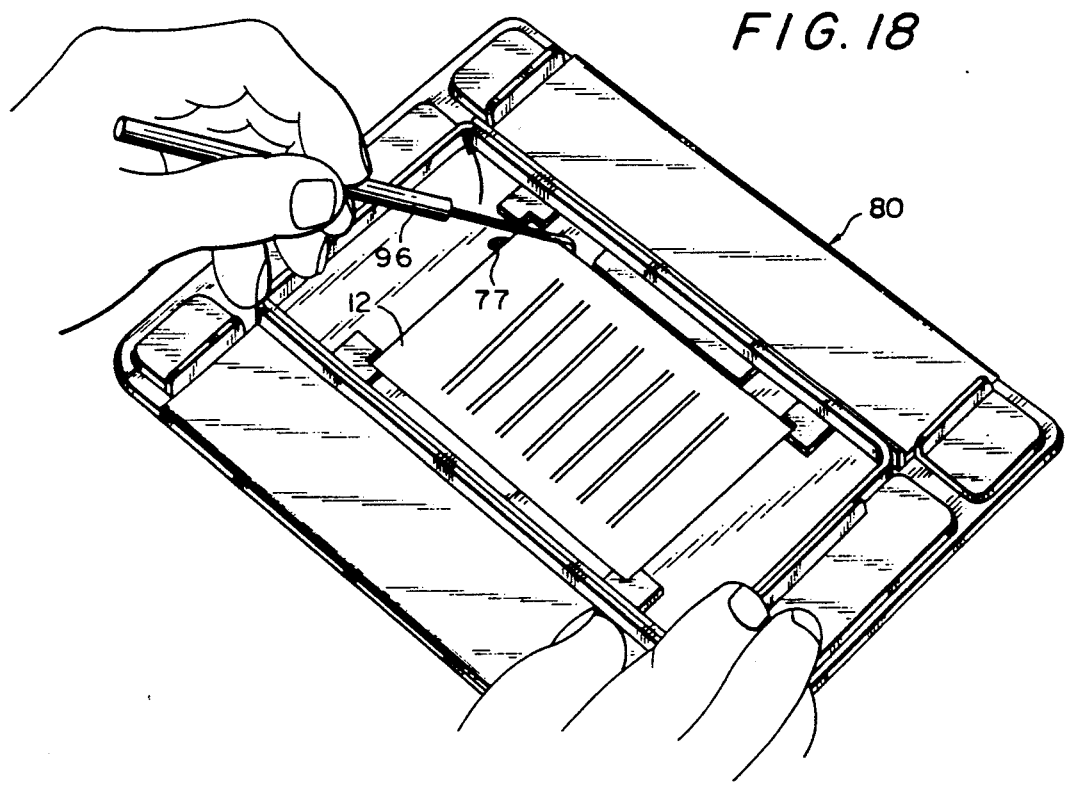
FIG. 18 is a perspective view showing use of a plate handling hook in removing a gel plate from a plate holder.

A gel plate is placed in a plate holder 70 and the trench former insert frame 180 is placed within the plate holder 70 as shown in FIGS. 17. The gel cutter 190 is then placed within the first pair of slots 186, 186a and the thumb plates 196 and 197 are pressed firmly down so that the plates 194, 195 cut the gel matrix 12. The tip 204 of the beak portion 202 of the gel displacement beak 200 is then placed into the open space 198 and the narrow strip of gel between the cutter blades is removed while the precisely positioned blades remain firmly pressed against the gel backing. This operation is then repeated for each of the slot pairs 186, 186a until eight precisely formed trenches are disposed in the gel plate 10. The plate with the trenches formed therein, suitable for use in the present invention, may then be removed from the plate holder 70 by means of the plate handling hook 96, as shown in FIG. 18. The tip 97 of the hook is placed under the edge of the gel plate 10 by means of one of the openings 77 in the bottom surface 72 of the plate holder 70, and lifted up and out of the plate holder 70 without actually touching the gel surface 12. In this manner a plurality of gels with formed trenches can be prepared for future use. Alternatively, the gel plate 10 can be left in the plate holder 70 for immediate use in an analytical procedure in accordance with the present invention.

EXAMPLE 2

Electrophoresis of Antigen

A gel plate having trenches formed as described in Example 1, or a gel plate which has been preformed in a factory with similar trenches, are soaked at least overnight in distilled water to remove the manufacturer's additives that might otherwise interfere with free diffusion of proteins in the gel matrix during the immunoprecipitation phase of the procedure. Each drained plate is resoaked for a minimum of 4 hrs. in 110 ml of calciumlactate-supplemented (1.5 mM) B-2 barbital buffer (0.0375M, pH 8.6, with 0.05% sodium azide) in order to re-equilibrate the plates with the desired buffer. A gel plate is then placed into plate holder 70 and held in place by means of guides 73 to 76. Underlay insert 86 is placed in recess 109 in the bottom surface 102 of plate holder frame 80, and the plate holder 70 is then placed into the plate holder frame between the vertical walls 104–107 thereof. As the gel is substantially transparent, as is the bottom surface of the plate holder 70, the underlay insert 86 can be seen through the gel, including guide marks 148 for the template 50. A preformed plastic template 50 is provided with the gel plates or with the equipment kit. The template 50 is preferably transparent or translucent. The plastic templates 50 have eight slots 52 therein through which serum samples can be applied, such as to leave a blade thin ribbon sample on each sample track. On the template used in this example, each of the slots are 6 mm wide with 4 mm between slots. The template can either be disposable or can be washed for reuse.

Before applying the template, the entire gel surface is blotted by an appropriate sheet of thin filter paper immediately prior to applying the template. As shown in FIG. 19, the template 50 is then carefully applied onto the gel plate 10 directly over the appropriate guide markings 148 seen in the underlay insert 86, such that the slots of the template are centered between trenches 14 with 1.5 mm between the side wall of each trench in the beginning of the template slot. A plastic burnishing rod 100 with a pliant tongue-shaped tip 101 is used to facilitate air-pocket free emplacement of the template over the blotted gel surface. Serum samples, prediluted two-fold with PBS, are then applied at 2.5 λ aliquots through each of the slits 52 of the template 50 by means of plastic applicator pen 98. The pen 98 preferably has a rounded tongue-shaped tip 99 used to streak the premeasured sample aliquots evenly over each application slit 52. Identical samples are applied in pairs to adjacent sample tracks. Thus, one serum sample is used on the first two tracks of the gel plate, another serum sample is used in the following two tracks, a third sample is applied to the next two tracks, and a fourth sample is applied to the final two tracks. The sample application template is carefully removed after all of the samples have diffused into the underlying gel matrix as thin ribbons.

EXAMPLE 3

Sample track transfer

Figure 8:
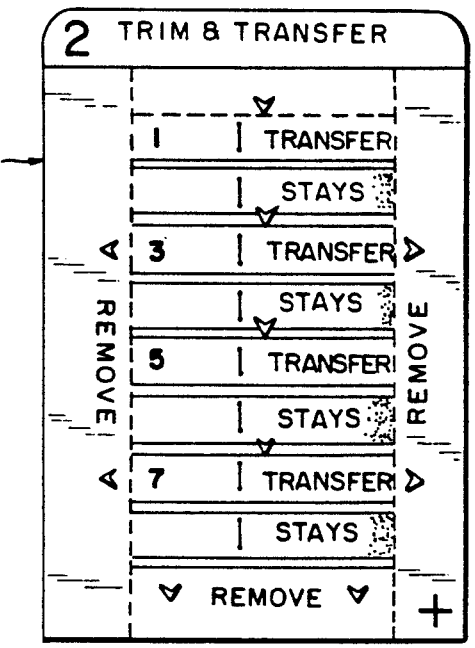
FIG. 8 is a plan view of a second underlay insert which may be used with the equipment and process of the present invention.

After the gel plates 10, having the serum sample applied thereon, have been removed from the plate holder 70 by means of the plate handling hook 96 (as shown in FIG. 18), the plates are transferred to an appropriate modular electrophoresis chamber, containing in each electrode reservoir 50 ml of the B-2 buffer previously used to re-equilibrate the gel plates prior to use. They are then subjected to a conventional electrophoresis operation for 12.5 min. at 125 Volts. The plate holder 70 is then removed from the plate holder frame 80 and the underlay insert 86 is replaced by underlay insert 88, as shown in FIG. 8. The plate holder 70 is then returned to the plate holder frame 80 and, after electrophoresis, the gel plate 10 is returned to the plate holder 70. The underlay insert 88 clearly shows the portions of the gel matrix 12 to be removed from the surface of the backing plate 11. First, by means of a suitably wide plate, the cathodal and anodal gel margins are scraped from the plate backing, as shown in FIG. 21. Next, the left and right margin inserts 82 and 84 are placed over the plate holder frame 80 with the bridges 128 resting upon the recently cleared portion of the backing plate 11. With the heels of the hands of the operator resting upon the margin inserts 82 and 84, thereby holding down the gel plate 10, as well as holding the position of the plate holder frame 80 on the support surface, a spatula 22 is used to remove the first sample track 32, as guided by the underlay insert 88. An individually identified spatula is used for each track to be transferred temporarily for direct protein staining. After the first sample track is removed (which does not necessarily have a trench at its forward surface), great care must be taken to insert the spatula within the trench so as not to touch the sidewalls of the sample tracks which remain. The transferred tracks are placed in individually identified staining/destaining chambers so that the electrophoretic migration patterns of the serum sample can be made permanently visible.

EXAMPLE 4

Antiserum Application

After one of each of the pairs of identical sample tracks have been transferred, the plate appears as four islands of gel matrix on the plate backing. The plate holder 70 is now removed from the plate holder frame 80 and underlay insert 88 is removed and replaced by underlay insert 90. Note that the underlay inserts may easily be removed by use of the plate handling hook 96, which may be inserted under the edge of the underlay inserts by means of opening 110 in the bottom surfaces of the plate holder frame 80. The plate holder 70 with the islands of gel material is then replaced into the plate holder frame. The precise location for application of the dabs of stopcock grease can clearly be seen on the underlay insert 90. Micro-dabs of stopcock grease (or other suitably pliant hydrophobic material) are applied to the vertical sidewalls 31 of the gel islands 32 on the backing 11 by means of an appropriate dispenser, such as a 6 mm syringe with a snubbed off 12 or 14 gauge tip. A discrete dab is applied near the end of each longitudinal sidewall in the positions shown on the underlay insert in order to contain the designated antisera along the respective upper and lower sidewalls of the non-transferred sample tracks.

Figure 10:
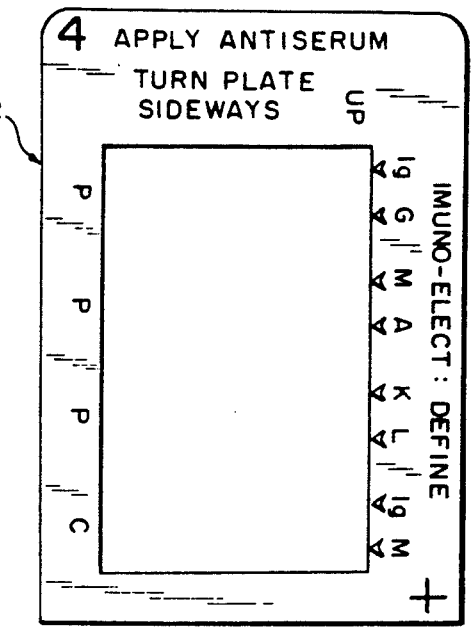
FIG. 10 is a plan view of a fourth insert, usable as an underlay or overlay, which may be used with the equipment and process of the present invention.

Next, the guide bar frame 160 is placed within the plate holder 70. Note that it is constructed so that nothing actually touches the islands of gel matrix which remain on the gel plate. The guide bars 166 are suspended above the islands of gel media. The underlay (overlay) insert 92, shown in FIG. 10, is then overlaid on top of the guide bar frame 160, as shown in FIG. 25. Alternatively, the insert 92 may be used as an underlay in the manner described above for inserts 86, 88, or 90. However, it can be seen better when used as an overlay in conjunction with the guide bar frame 160. When the guide bar frame is not being used and the antiserum is being applied unaided by a guide bar frame, then the insert 92 should replace the insert 90 as the underlay insert below the plate holder 70 in order clearly to indicate the antiserum protocol.

A micro-dispenser 210 with a needle 212 is used to streak the designated antisera evenly along each upper and lower sample track sidewall delineated by the micro-dabs of stopcock grease. The plate is preferably turned sideways with the needle being guided by being pressed against the bevel 168 of the appropriate guide bar 166, while the dispenser 210 is guided along the guide bar with the antiserum being dispensed along the entire length of the sidewall between the micro-dabs. To maintain the integrity of the vertical sidewalls 31, the tip of the dispensing needle should never actually contact the gel itself. Preferably, a 7.5λ aliquot of precipitating antiserum of desired specificity is applied to each sidewall. The hydrophobic pliant stopcock grease maintains the antiserum in line so that the antiserum is unidirectionally absorbed into the delineated segments of gel sidewall by simple capillary action. Eight different antisera may be used on each plate, one on each exposed sidewall 31.

The specific antisera which are used in any given assay will depend on the particular protocol being run. Generally, these assays are for the detection and characterization of monoclonal immunoglobulin components. If no abnormal banding has been seen by direct inspection of an initial serum protein electrophoresis pattern (SPEP), or an SPEP has not yet been completed, then a screening electrophoretic-immunoelectrophoretic analysis will be performed. In a screening analysis each sample track has a polyspecific anti-total Ig applied to one exposed side wall and a monospecific anti-IgM applied to the opposite side wall. The polyspecific anti-total Ig antiserum must include demonstrable precipitating activity against IgG, IgM, IgA, κ, and λ. Three of the sample tracks can screen sera of different patients. The fourth sample track is always a normal control serum.

When performing the screening analysis, the underlay insert 91, as shown in use in FIG. 25, is used. "IMMUNO-ELECT" is an abbreviation of "immunoelectrophoretic-electrophoretic analysis". The symbol "Ig" directed toward one side wall of each sample track stands for the polyspecific anti-total Ig which is to be applied thereto. The symbol "M" stands for monospecific anti-IgM which is applied to the track to which the M is pointed. At the opposite side of the opening 93 are the symbols "P" and "C". The "P" stands for patient and the "C" stands for control.

If abnormal electrophoretic banding and/or abnormal immunoprecipitation arcs are seen in the immunoelectrophoretic-electrophoretic screening, then an expanded analysis is conducted in order to define the specific abnormality. For this purpose the "IMMUNO-ELECT: DEFINE" overlay 92, shown in FIG. 10, is used. In this protocol, serum from the same patient is used on three pairs of the sample tracks and the fourth pair of sample tracks is a control. To the side wall toward which the mark "G" is directed on the overlay 92, is applied monospecific anti-IgG. To the side wall marked "M" is applied monospecific anti-IgM, to the side wall marked "A" is applied monospecific anti-IgA, to the side wall marked "K" is applied monospecific anti-κ, to the side wall marked "L" is applied monospecific anti-λ. For the control, the same polyspecific anti-total Ig and monospecific anti-IgM, as is used in the screen protocol, are used. Other antiserum options include:

(a) anti-fibrinogen, if an abnormal band is seen near the origin;

(b) anti-C-reactive protein, if an abnormal small band is seen in the gamma region; or (c) anti-transferin, if an abnormally prominent beta band is seen.

Other protocols may, of course, also be run using this procedure. For example, if the heavy chain and/or light chain typing of an apparently monoclonal Ig component is equivocated by polyclonal background Ig, then the problematic Ig bands can first be isolated by stepwise fractionation with polyethylene glycol with an appropriate immunoelectrophoresis-electrophoresis analysis being conducted with any polyethylene glycol fraction in which the problematic Ig bands are disproportionately amplified. Similarly, if anti-κ or anti-λ homogeneity is seen without matching heavy chain activity in an expanded whole serum analysis or polyethylene glycol fraction, and no corresponding κ or λ band is disproportionately amplified in a concentrated urine sample, the analysis can be expanded to include monospecific anti-IgD and monospecific anti-IgE. Further fractionation options to aid and abet the characterization of problematic Ig components include stepwise ammonium sulphate precipitation, DEAE iron exchange chromatography, agarose gel electro-purification, and gel-filtration chromatography.

EXAMPLE 5

Incubation and Transfer

After appropriate antiserum has been applied to each vertical sidewall, the plate 10 is removed from the plate holder 70 and placed into an appropriate incubation chamber. After incubation, the plate is placed into a soaking-out chamber to wash out the background protein prior to drying and staining of the immunoprecipitation patterns. The hydrophobic dabs of stopcock grease can be scraped away conveniently while the plates are thus immersed. Prior to staining the washed and dried plates, residual stopcock grease can be wiped away with a soft tissue paper. The plates with the immunoprecipitation patterns thereon are then dried and stained in a conventional manner.

After staining the immunoprecipitation patterns, the L-shaped transfer spatulas 172 are used for remounting each zonal-protein track in exactly its original position, as is shown in FIG. 27. This provides an exactly matching zonal protein reference pattern for each sample track containing immunoprecipitation patterns. The gel plates having the remounted tracks are then preferably placed on appropriately annotated mounting sheets for convenient readily retrievable filing of the finally reassembled and dried plates.

The method of the present invention, by which an exactly corresponding electrophoretic pattern is juxtaposed with each pair of immunoprecipitation patterns, greatly facilitates definitive interpretation of the completed plates. The procedure, which is further facilitated through use of plates with preformed trenches can be performed faster and more economically than any of the alternative procedures currently available for immunoelectrophoretic analysis. The prozone-minimizing 90 degree angle of interception between the laterally diffusing linear fronts of antigen and closely opposed linear fronts of diffusion antiserum strikingly reduces both the incubation time and the amounts of antiserum ordinarily required for the formation of definitive immunoprecipitation patterns. In addition, the prozone-minimizing double-immunodiffusion-gradient relationship of antigen to antibody permits clear-cut immunoprecipitation patterns to form over a broad range of very low to very high concentrations of antigen. This is the case even with the comparatively small amounts of standard grade precipitating antiserum routinely employed in the procedure (e.g., 7.5 lambda per gel sidewall with thin-layer 75×100 mm plates).

As an example of the type of buffers and agarose gel that can be used in the present invention, barbital buffer B-2 (0.075M, pH 8.6, containing 0.1% w/v sodium azide) may be mixed with an equal volume of 3.0 mM aqueous calcium lactate solution. Agarose gels may be prepared by dissolving SeaKem ME agarose (Marine Colloids, Rockland, Me.) at 0.5% w/v concentration in the same buffer. This composition represents a lower ionic-strength buffer system which minimizes heat buildup during operation yet still permits a 15- to 20-minute rapid electrophoretic separation of a distinct serum alpha-1-globulin band from albumin, following a 15- to 20-mm migration of the albumin band from the application point.

Using the assays as described above, it is possible rapidly to identify diagnostically important pathological components in serum or other body fluids, such as urine or cerebrospinal fluid.

The process of the present invention permits use of increased numbers of samples per plate while still permitting an adjacent reference electrophoresis pattern. The use of the pliant hydrophobic material permits use of less antiserum because the antiserum migrates only in one direction and thus is not diluted as much as in conventional processes.

The foregoing description of the specific embodiments so fully reveals the general nature of the invention that others can readily modify and/or adapt such specific embodiments for various applications without departing from the generic concept. Any such adaptations and modifications are intended to be embraced within the meaning and range of equivalents of the disclosed embodiments. It is to be understood that the phraseology and terminology employed herein are for the purpose of description and not of limitation.

What is claimed is:

1. A kit for facilitating combined electrophoretic-immunoelectrophoretic analysis, comprising:
   1) a plate holder comprising side walls defining a predetermined perimeter, gel-support surface means for supporting a gel plate, and guide means for guiding a gel plate into a predetermined position on said gel-support surface means; and
   2) a plate holder frame comprising guide wall means having an inner perimeter corresponding to the outer perimeter of said plate holder side walls for holding said plate holder therewithin, plate holder support surface means for supporting said plate holder within said wall means, and a peripheral surface disposed outside of said guide wall means, said peripheral surface being an extension of said plate holder support surface means, said peripheral surface extending beyond said guide wall means for a distance sufficient to serve as a hand support when in use.

2. A kit in accordance with claim 1, and further including left and right gel plate holding support means for resting on said peripheral surface of said plate holder frame and simultaneously holding a gel plate in place on said plate holder when in use, each of said gel plate holding support means comprising a hand support surface sized and dimensioned so as to rest upon a portion of said peripheral surface of said plate holder frame, a plate contact means for resting upon a gel plate when a gel plate is in place in said plate holder frame, and bridge means connecting said hand support means and said gel holding means for bridging said side walls of said plate holder and said guide wall means of said plate holder frame.

3. A kit in accordance with claim 1, and further including a guide bar frame comprising side wall means having an outer perimeter sized and dimensioned so as to precisely fit within the inner perimeter of the side walls of said plate holder, and guide bar means traversing said guide bar frames so as to be suspended above a gel plate when in place on said gel holder when said guide bar frame is disposed within said plate holder, said guide bar means being precisely disposed in a predetermined position so as to facilitate a step of the electrophoretic-immunoelectrophoretic analysis method to be performed by means of the kit.

4. A kit in accordance with claim 1, and further including spatula means for transferring tracks of gel matrix to and from a gel plate when the kit is in use.

5. A kit in accordance with claim 1, and further including a trench former insert frame comprising perimeter walls having an outer perimeter sized and dimensioned so as to fit precisely within the inner perimeter of the side walls of said plate holder, and two matching rows of multiple slots disposed on opposing portions of said perimeter walls, each of said pairs of slots being precisely disposed in a predetermined position with respect to a gel plate held in said plate holder when said trench former insert frame is disposed in said plate holder;

a double bladed trench cutter comprising two gel cutting blades, two blade support means disposed parallel to and in predetermined distance from one another, each having one of said cutting blades mounted thereon on the inside surface facing the other blade support means, the blade portion of said cutting blades extending out beneath said blade support means, for supporting said blades in a predetermined position, and two thumb plate means connected to said blade support means on the side thereof opposite the side from which said blades extend and fixing said blade support means and the supported blades such that said blades are held parallel to one another with a fixed predetermined separation therebetween and such that the space between said blades between said thumb plate means remains completely accessible from the side of said blade support means opposite the side from which said blades extend, and wherein the outside dimensions of said blade support means precisely correspond to the dimensions of said multiple slots so as to precisely fit therewithin when in use; and a gel displacement beak having a width exactly equal to the space between said blades, said gel displacement beak having a beak portion tapering to a tip at one end and having a handle portion at the other end.

6. A kit in accordance with claim 1, and further including:

a trench former frame shaped and dimensioned so as to cooperate with said plate holder and be maintained in a predetermined position with respect to a gel plate supported by said plate holder when in use;

a double bladed trench cutter comprising
   (a) two gel cutting blades
   (b) two blade support means disposed parallel to and at a predetermined distance from one another, each having one of said cutting blades mounted thereon on the inside surface facing the other blade supporting means, the blade portion of said cutting blades extending out beneath said blade support means, for supporting said blades in a predetermined position, and
   (c) connecting means connected to said blade support means and fixing said blade support means and the supported blades such that the space between said blades remains accessible from the side of said blade support means opposite the side from which said blades extend; and positioning means associated with said trench former frame and said trench cutter for ensuring that said trench cutter is positioned on said trench former frame at a predetermined position with respect to the gel plate to be trenched when in use.

7. A kit in accordance with claim 1, wherein said plate holder support surface means has a recess therein sized and dimensioned so as to receive and hold in position an underlay insert having printed matter which is desired to be seen through said plate holder and any gel plate disposed thereon when in use, and wherein said gel support surface means of said plate holder is substantially transparent.

8. A kit in accordance with claim 7, and further including a plurality of underlay inserts sized and dimensioned so as to fit and be held in said recess of said plate holder support surface means, each of said inserts showing or explaining one or more steps of the combined electrophoretic-immunoelectrophoretic analysis process which is to be performed using the kit.

9. A kit in accordance with claim 1, wherein said gel support surface means of said plate holder includes an opening therein disposed so as to be traversed by an edge of a gel plate when in position in said plate holder.

10. A kit in accordance with claim 9, and further including a plate handling hook including a handle at one end and hook means at the other end for insertion into the opening in the gel support surface means of said plate holder such that the hook means can reach beneath a gel plate in place on said plate holder when in use and facilitate the lifting of the gel plate from said plate holder.

11. A kit in accordance with claim 1, and further including a plurality of gel plates each comprising:
 a substantially rigid, electrically non-conducting, non-porous backing; and
 a layer of a substantially non-seiving neutral electrophoresis matrix adhered to said backing, said matrix having a plurality of parallel trenches therein extending linearly from points at or near the edges of the gel, said trenches having a width of about 0.5 to about 3 mm and being spaced from one another at a distance approximately equal to the width of a desired electrophoresis track, thereby dividing the gel into a plurality of tracks, no other gaps in said matrix being present, the side walls of said trenches being perpendicular to said backing and extending vertically all the way to said backing.

12. A kit in accordance with claim 11, and further including a template having a number of colinear slits, said slits being arranged such that when said template is disposed on said gel plate, each said slit is perpendicular to the longitudinal direction of said trenches and disposed in a predetermined position between two adjacent trenches.

13. A kit for facilitating the formation of precisely disposed trenches in a gel plate, comprising:
 a trench former insert frame comprising perimeter walls and two matching rows of multiple slots disposed on opposing portions of said perimeter walls each of said pairs of slots being precisely disposed in a predetermined position;
 a double bladed trench cutter comprising two gel cutting blades, two blade support means disposed parallel to and in predetermined distance from one another, each having one of said cutting blades mounted thereon on the inside surface facing the other blade support means, the blade portion of said cutting blades extending out beneath said blade support means, for supporting said blades in a predetermined position, and two thumb plate means connected to said blade support means on the side thereof opposite the side from which said blades extend and fixing said blade support means and the supported blades such that said blades are held parallel to one another with a fixed predetermined separation therebetween and such that the space between said blades between said thumb plate means remains completely accessible from the side of said blade support means opposite the side from which said blades extend, and wherein the outside dimensions of said blade support means precisely correspond to the dimensions of said multiple slots so as to precisely fit therewithin when in use; and
 a gel displacement beak having a width exactly equal to the space between said blades, said gel displacement beak having a beak portion tapering to a tip at one end and having a handle portion at the other end.

14. A kit in accordance with claim 13, and further including a plate holder comprising side walls defining a predetermined perimeter, the inner circumference of which exactly corresponds to the outer perimeter of the perimeter walls of said trench former insert frame, gel support surface means for supporting a gel plate, and guide means for guiding a gel plate into a predetermined position on said gel support surface means.

15. A kit for use in preparing a trenched gel plate, comprising:
 a trench former frame which is disposed in a predetermined position with respect to the gel plate to be trenched when in use;
 a double bladed trench cutter comprising
  a) two gel cutting blades,
  b) two blade support means disposed parallel to and at a predetermined distance from one another, each having one of said cutting blades mounted thereon on the inside surface facing the other blade supporting means, the blade portion of said cutting blades extending out beneath said blade support means, for supporting said blades in a predetermined position, and
  c) connecting means connected to said blade support means and fixing said blade support means and the supported blades such that the space between said blades remains accessible from the side of said blade support means opposite the side from which said blades extend; and
 positioning means associated with said trench former frame and said trench cutter for ensuring that said trench cutter is positioned on said trench former frame at a predetermined position with respect to the gel plate to be trenched when in use.

16. A kit in accordance with claim 15, wherein said positioning means comprises two matching rows of multiple slots disposed on opposing portions of said trench former frame, each of said pairs of slots being precisely disposed in a predetermined position with respect to the gel plate to be trenched when in use, and wherein the outside dimensions of said blade support means of said trench cutter precisely corresponds to the dimensions of said multiple slots so as to precisely fit therewithin when in use.

17. A kit in accordance with claim 15, wherein said connecting means comprise two thumb plate means connected to said blade support means on the side thereof opposite the side from which said blades extend and fixing said blade support means and the supported blades such that said blades are held parallel to one another with a fixed predetermined separation therebetween and such that the space between said blades between said thumb plate means remains completely accessible from the side of said blade support means opposite the side from which said blades extend.

* * * * *